United States Patent [19]

Reff

[11] Patent Number: 6,017,733
[45] Date of Patent: *Jan. 25, 2000

[54] IMPAIRED DOMINANT SELECTABLE MARKER SEQUENCE AND INTRONIC INSERTION STRATEGIES FOR ENHANCEMENT OF EXPRESSION OF GENE PRODUCT AND EXPRESSION VECTOR SYSTEMS COMPRISING SAME

[75] Inventor: Mitchell E. Reff, San Diego, Calif.

[73] Assignee: IDEC Pharmaceuticals Corporation, San Diego, Calif.

[*] Notice: This patent is subject to a terminal disclaimer.

[21] Appl. No.: 09/013,092

[22] Filed: Jan. 26, 1998

Related U.S. Application Data

[63] Continuation of application No. 08/484,334, Jun. 7, 1995, Pat. No. 5,733,779, which is a continuation of application No. 08/147,696, Nov. 3, 1993, Pat. No. 5,648,267, which is a continuation-in-part of application No. 07/977,691, Nov. 13, 1992, abandoned.

[51] Int. Cl.⁷ .................................................... C12P 21/02
[52] U.S. Cl. ........................................ 435/69.6; 435/320.1
[58] Field of Search .............................. 435/320.1, 69.1, 435/69.6

[56] References Cited

FOREIGN PATENT DOCUMENTS

0451216 B1  10/1991  European Pat. Off. .
0682040 A1  11/1995  European Pat. Off. .

OTHER PUBLICATIONS

Yenofsky, 1990, *Natl. Acad. Sci.*, 87:3435–3439.
Abrams, 1989, *J. Biol. Chem.*, 264:14016–14021.
Kozak, 1989, *J. Biol. Chem.*, 108:229–241.
Kozak, 1986, *Proc. Natl. Acad. Sci.*, 83:2850–2854.
Kozak, 1987, *Mol. Cell Biol.*, 7(10):3438–3445.
Kozak, 1984, *Mol. Cell Biol.*, 9(11):5073–5084.
Niwa, 1991, Gene, 108:193–200.
Sambrook et al, 1989, Molecular Cloning: A Laboratory Manual, Colo. Springs/Harbor Press, Col. Spring, Harbor, NY.
Hartman et al, 1988, *Proc. Natl. Acad. Sci.*, 85:8047–8051.
Barnett et al, "Antibody Production in Chinese Hamster Ovary Cells Using an Impaired Selectable Marker", *American Chemical Society*, 1995.

Potter et al, "Enhancer–dependent expression of human K immunoglobulin genes introduced into mouse pre–B lymphocytes by electroporation", *Proc. Natl. Acad. Sci. USA*, vol. 81, pp. 7161–7165, Nov. 1984.

Yoshimura et al, "Different Activities of Viral Enhancer Elements before and after Stable integration of Transfected DNAs", *Molecular and Cellular Biology*, pp. 1296–1299, Mar. 1987.

von Knebel Doeberitz et al, "Influence of chromosomal integration on glucocorticoid–regulated transcription of growth–stimulating papillomavirus genes E6 and E7 in cervical carcinoma cells", *Proc. Natl. Acad. Sci. USA*, vol. 88, pp. 1411–1415, Feb. 1991.

Conklin et al, "Varied Interactions between Proviruses and Adjacent Host Chromatin", *Molecular and Cellular Biology*, pp. 3999–4007, Nov. 1986.

Al–Shawi et al, "Expression of a Foreign Gene in a Line of Transgenic Mice Is Modulated by a Chromosomal Position Effect", *Molecular and Cellular Biology*, pp. 1192–1198, Mar. 1990.

*Primary Examiner*—James Ketter
*Attorney, Agent, or Firm*—Burns, Doane, Swecker & Mathis, L.L.P.

[57] ABSTRACT

Disclosed herein are fully impaired consensus Kozak sequences which are most typically used with dominant selectable markers of transcriptional cassettes which are a part of an expression vector, These vectors are most typically utilized in the expression of proteins in mammalian expression systems. As defined, disclosed and claimed herein, a "fully impaired consensus Kozak" comprises the following sequence:

```
-3        +1
Pyxx ATG Pyxx
``` where: "x" is a nucleotide selected from the group consisting of adenine (A), quanine (G), cytosine (C) or thymine (T)/uracil (U); "Py" is a pyrimidine nucleotide, ie C or T/U; "ATG" is a codon encoding for the amino acid methionine, the so-called "start" codon; and −3 and +1 are directional reference points vis-a-vis ATG, ie −3 is meant to indicate three nucleotides upstream of ATG and +1 is meant to indicate one nucleotide downstream of ATG. Dominant selectable markers further comprising artificial intronic insertion regions are further disclosed.

10 Claims, 6 Drawing Sheets

FIG. 1

Neomycin phosphotransferase gene

```
                             Cla I         -3        +1
TCAE 5.2  TTGGGAGCTTGG   ATCGAT  CC A cc  ATG Gtt
                                              Met Val
ANEX  1   TTGGGAGCTTGG   ATCGAT  CC T cc  ATG Ctt
                                              Met Leu
ANEX  2   CCaGCATGgAGGA  ATCGAT  CC T cc  ATG Ctt
                                              Met Leu
```

IMPAIRED DOMINANT SELECTABLE MARKER SEQUENCE AND INTRONIC INSERTION STRATEGIES FOR ENHANCEMENT OF EXPRESSION OF GENE PRODUCT AND EXPRESSION VECTOR SYSTEMS COMPRISING SAME

RELATED APPLICATIONS

This application is a continuation of application Ser. No. 08/484,344, filed Jun. 7, 1995, now U.S. Pat. No. 5,733,779, in turn a continuation of application Ser. No. 08/147,696, filed Nov. 3, 1993, now U.S. Pat. No. 5,648,267, in turn a continuation-in-part of application Ser. No. 07/977,691, filed Nov. 3, 1992, now abandoned. This patent document is related to "THERAPEUTIC APPLICATION OF CHIMERIC ANTIBODY TO HUMAN B LYMPHOCYTE RESTRICTED DIFFERENTIATION ANTIGEN FOR TREATMENT OF B CELL LYMPHOMA," having U.S. Ser. No. 07/978,891, filed Nov. 13, 1992 (pending), and "THERAPEUTIC APPLICATION OF CHIMERIC AND RADIOLABLED ANTIBODIES TO HUMAN B LYMPHOCYTE RESTRICTED DIFFERENTIATION ANTIGEN FOR TREATMENT OF B CELL LYMPHOMA", having U.S. Ser. No. 08/149,099, filed simultaneously herewith. This patent document is related to commonly assigned U.S. Ser. No. 07/912,292 and entitled "RECOMBINANT ANTIBODIES FOR HUMAN THERAPY," filed Jul. 10, 1992. These documents are incorporated herein by reference. 37 C.F.R. §1.74(d)/(e) COPYRIGHT NOTICE A portion of the disclosure of this patent document contains material which is subject to copyright protection. The copyright owner does not object to the reproduction by anyone of the patent document or the patent disclosure, as it appears in the Patent and Trademark Office patent files or records, but otherwise reserves all copyright rights whatsoever.

FIELD OF THE INVENTION

References cited in this patent document are presented for the information contained therein as such information elucidates the disclosed invention; these references are not admitted to be statutory "prior art" and the inventor reserves the right to claim prior inventorship vis-a-vis these references.

Disclosed herein are mammalian expression vectors useful in recombinant DNA technology. More particularly, the disclosed invention is directed to selectable marker nucleic acid sequences utilized in conjunction with such vectors, and in particular, to impaired selectable marker sequences comprising artificial intronic insertion regions which enhance expression of a desired gene product.

BACKGROUND OF THE INVENTION

It has been well over a decade since Cohen and Boyer first reported the use of bacterial plasmids as molecular cloning vectors; this marked the beginning of a new era in molecular biology and, historically, laid the foundation for what has been termed the "biotechnology industry." Cohen and Boyer's cloning vector, pSC101, relative to the cloning vectors in circulation today, seems almost quaint—insertion of foreign DNA fragments into pSC101 was limited to a single restriction enzyme cleavage site and to *Escherichia coli* as a host. During the past decade, the art has had access to hundreds of molecular cloning vectors having nearly as much applicability and diversity as the number of vectors. Irrespective of the variety of such vectors, the typical objective remains the same: increased availability of a protein of interest that ordinarily are produced naturally in minute quantities.

As noted, the advent of the biotechnology industry has allowed for the production of large quantities of proteins. Proteins are the essential constituents of all living cells and proteins are comprised of combinations of 20 naturally occurring amino acids; each amino acid molecule is defined ("encoded") by groupings ("codons") of three deoxyribonucleic add ("DNA") molecules; a string of DNA molecules ("DNA macromolecule") provides, in essence, a blueprint for the production of specific sequences of amino acids specified by that blueprint. Intimately involved in this process is ribonucleic acid ("RNA"); three types of RNA (messenger RNA; transfer RNA; and ribosomal RNA) convert the information encoded by the DNA into, eg a protein. Thus, genetic information is generally transferred as follows: DNA→RNA→protein.

In accordance with a typical strategy involving recombinant DNA technology, a DNA sequence which encodes a desired protein material ("cDNA") is identified and either isolated from a natural source or synthetically produced. By manipulating this piece of genetic material, the ends thereof are tailored to be ligated, or "fit," into a section of a small circular molecule of double stranded DNA. This circular molecule is typically referred to as a "DNA expression vector," or simply a "vector." The combination of the vector and the genetic material can be referred to as a "plasmid" and the plasmid can be replicated in a prokaryotic host (ie bacterial in nature) as an autonomous circular DNA molecule as the prokaryotic host replicates. Thereafter, the circular DNA plasmid can be isolated and introduced into a eukaryotic host (ie mammalian in nature) and host cells which have incorporated the plasmid DNA are selected. While some plasmid vectors will replicate as an autonomous circular DNA molecule in mammalian cells, (eg plasmids comprising Epstein Barr virus ("EBV") and Bovine Papilloma virus ("BPV") based vectors), most plasmids including DNA vectors, and all plasmids including RNA retroviral vectors, are integrated into the cellular DNA such that when the cellular DNA of the eukaryotic host cell replicates, the plasmid DNA will also replicate. Accordingly, as eukaryotic cells grow and divide, there is a corresponding increase in cells containing the integrated plasmid which leads to the production ("expression") of the protein material of interest. By subjecting the host cells containing the plasmid to favorable growth conditions, significant amounts of the host, and hence the protein of interest, are produced. Typically, the Chinese Hamster Ovary ("CHO") cell line is utilized as a eukaryotic host cell, while *E. coli* is utilized as a prokaryotic host cell.

The vector plays a crucial role in the foregoing— manipulation of the vector can allow for variability as to where the cDNA is inserted, means for determining whether the cDNA was, in fact, properly inserted within the vector, the conditions under which expression of the genetic material will or will not occur, etc. However, most of the vector manipulations are geared toward a single goal—increasing expression of a desired gene product, ie protein of interest. Stated again, most vector manipulation is conducted so that an "improved" vector will allow for production of a gene product at significantly higher levels when compared to a "non-improved" vector. Thus, while certain of the features/ aspects/characteristics of one vector may appear to be similar to the features/aspects/characteristics of another vector, it is often necessary to examine the result of the overall goal of the manipulation—improved production of a gene product of interest.

While one "improved" vector may comprise characteristics which are desirable for one set of circumstances, these characteristics may not necessarily be desirable under other circumstances. However, one characteristic is desirable for all vectors: increased efficiency, ie the ability to increase the amount of protein of interest produced while at the same time decreasing the number of host cells to be screened which do not generate a sufficient amount of this protein. Such increased efficiency would have several desirable advantages, including reducing manufacturing costs and decreasing the time spent by technicians in screening for viable colonies which are expressing the protein of interest. Accordingly, what would be desirable and what would significantly improve the state of the art are expression vectors with such efficiency characteristics,

SUMMARY OF THE INVENTION

The invention disclosed herein satisfies these and other needs. Disclosed herein are fully impaired consensus Kozak sequences which are most typically used with dominant selectable markers of transcriptional cassettes which are a part of an expression vector; preferably, the dominant selectable marker comprises either a natural intronic insertion region or artificial intronic insertion region, and at least one gene product of interest is encoded by DNA located within such insertion region.

As used herein, a "dominant selectable marker" is a gene sequence or protein encoded by that gene sequence; expression of the protein encoded by the dominant selectable marker assures that a host cell transfected with an expression vector which includes the dominant selectable marker will survive a selection process which would otherwise kill a host cell not containing this protein. As used herein, a "transcriptional cassette" is DNA encoding for a protein product (eg a dominant selectable marker) and the genetic elements necessary for production of the protein product in a host cell (ie promoter; transcription start site; polyadenylation region; etc.). These vectors are most preferably utilized in the expression of proteins in mammalian expression systems where integration of the vector into host cellular DNA occurs. Beneficially, the use of such fully impaired consensus Kozak sequences improves the efficiency of protein expression by significantly decreasing the number of viable colonies while at the same time, significantly increasing the amount of protein expressed by such viable colonies. As used herein, a "natural intronic insertion region" is a region of DNA naturally present within a gene in this case, typically a dominant selectable marker, which can be utilized for insertion of DNA encoding a gene product of interest; an "artificial intronic insertion region" is a region of DNA which is selectively created in a gene (again, most typically, a dominant selectable marker) which can be utilized for insertion of DNA encoding a gene product of interest. Information regarding intronic positioning is described in Abrams, J. M. et al. "Intronic Positioning Maximizes Co-expression and Co-amplification of Nonselectable Heterologous Genes." *J. Bio. Chem.*, 264124:14016 (1989), and U.S. Pat. No. 5,043,270 (both documents being incorporated herein by reference).

As defined, disclosed and claimed herein, a "fully impaired consensus Kozak" comprises the following sequence:

```
-3      +1
Pyxx ATG Pyxx
``` where: "x" is a nucleotide selected from the group consisting of adenine (A), quanine (G), cytosine (C) or thymine (T)/ uracil (U); "Py" is a pyrimidine nucleotide, ie C or T/U; "ATG" is a codon encoding for the amino acid methionine, the so-called "start" codon; and −3 and +1 are directional reference points vis-a-vis ATG, ie −3 is meant to indicate three nucleotides upstream of ATG and +1 is meant to indicate one nucleotide downstream of ATG.

Preferably, the fully impaired consensus Kozak is part of a methionine start codon that initiates translation of a dominant selectable marker portion of a transcriptional cassette which is part of an expression vector. Preferred dominant selectable markers include, but are not limited to: herpes simplex virus thymidine kinase; adenosine deaminase; asparagine synthetase; Salmonella his D gene; xanthine guanine phosphoribosyl transferase; hygromycin B phosphotransferase; and neomycin phosphotransferase. Most preferably, the dominant selectable marker is neomycin phosphotransferase.

In particularly preferred embodiments of the invention, at least one out-of-frame start codon (ie ATG) is located upstream of the fully impaired consensus Kozak start codon, without an in-frame stop codon being located between the upstream start codon and the fully impaired consensus Kozak start codon. As used herein, the term "stop codon" is meant to indicate a codon which does not encode an amino acid such that translation of the encoded material is terminated; this definition includes, in particular, the traditional stop codons TAA, TAG and TGA. As used herein, the terms "in-frame" and "out-of-frame" are relative to the fully impaired consensus Kozak start codon. By way of example, in the following sequence:

```
            -3       +1
GAC CAT GGC Cxx ATG Cxx
``` the underlined portion of the sequence is representative of a fully impaired consensus Kozak (where "x" represents a nucleotide) and the codons GAC, CAT and GCC are "in-frame" codons relative to the ATG start codon. The above-lined nucleotides represent an "out-of-frame" start codon which is upstream of the fully impaired consensus Kozak start codon. Preferably, the out-of-frame start codon is within about 1000 nucleotides upstream of the fully impaired consensus Kozak start codon, more preferably within about 350 nucleotides upstream of the fully impaired consensus Kozak start codon, and most preferably within about 50 nucleotides upstream of the fully impaired consensus Kozak start codon. Preferably, the out-of-frame start codon is a part of a consensus Kozak. By way of example, the sequence set forth above satisfies this criteria: the −5 nucleotide is a purine (G); nucleotide −6, −7 and −8 encode an out-of-frame start codon (ATG); and nucleotide −11 is a purine (A).

Additionally, utilization of a fully impaired consensus Kozak within a secondary structure (ie a so-called "stem-loop" or "hairpin") is beneficially viable to impairment of translation of the protein encoded by the dominant selectable number. In such an embodiment, the start codon of the fully impaired consensus Kozak is most preferably located within the stem of a stem loop.

Particularly preferred expression vectors which incorporate these aspects of the invention disclosed herein are referred to as "TCAE," and "ANEX" and "NEOSPLA" vectors; particularly preferred vectors are referred to as ANEX 1, ANEX 2 and NEOSPLA3F.

These and other aspects of the invention disclosed herein will be delineated in further detail in the sections to follow.

BRIEF DESCRIPTION OF THE DRAWINGS

FIG. 1 provides the relevant portion of a consensus Kozak and several particularly preferred fully impaired consensus Kozak sequences;

DETAILED DESCRIPTION OF PREFERRED EMBODIMENTS

Figure 2:
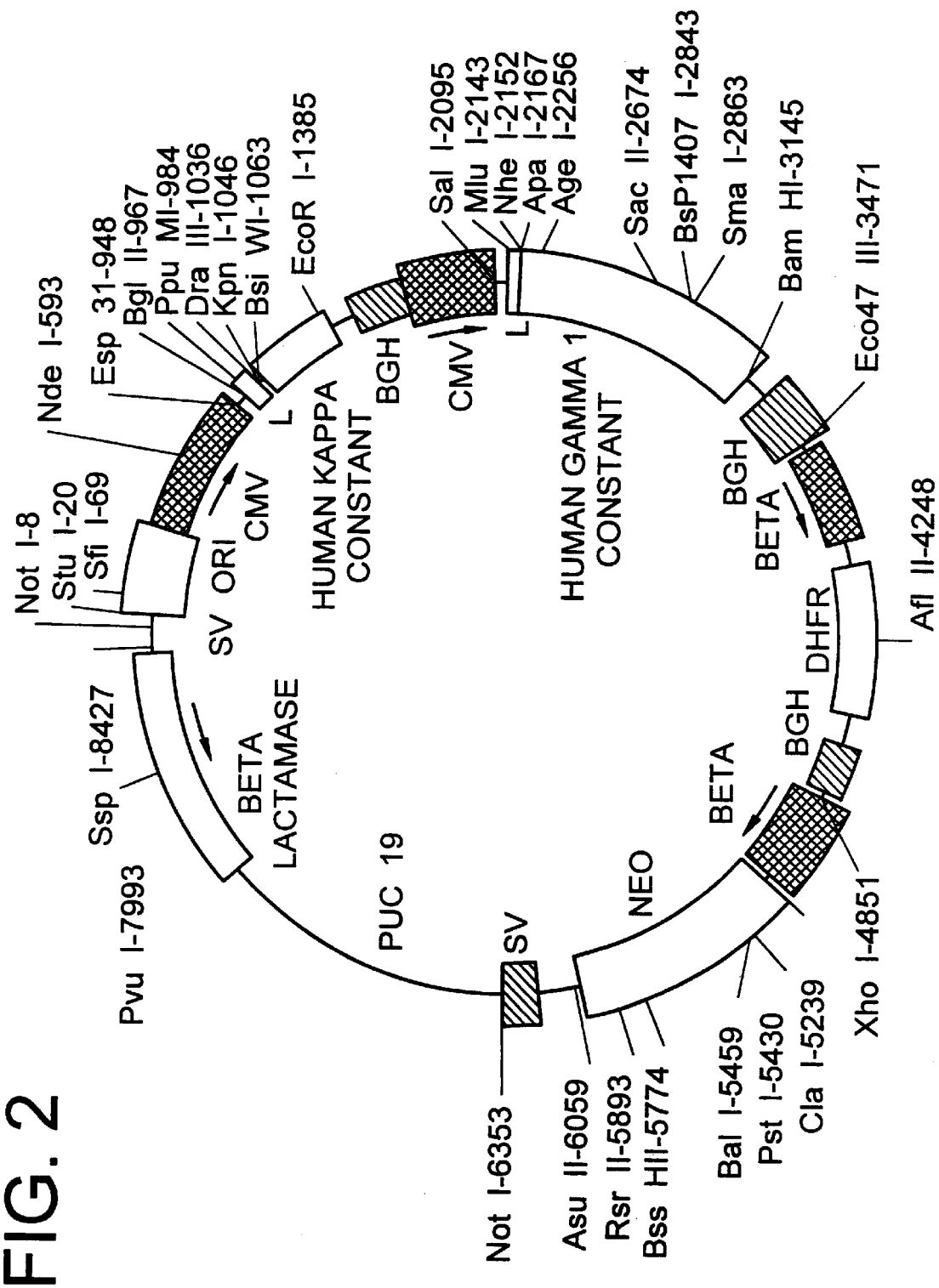
FIG. 2 provides a diagrammatic representation of the vectors TCAE 5.2 and ANEX 1 (TCAE 12) designed for expression of mouse/human chimeric immunoglobulin, where the immunoglobulin genes are arranges in a tandem configuration using neomycin phosphotransferase as the dominant selectable marker.

Disclosed herein are nucleic acid sequence arrangements which impair translation and initiation of, most preferably, dominant selectable markers incorporated into mammalian expression vectors and which are preferably, but not necessarily, co-linked to an encoding sequence for a gene product of interest. Preferably, the dominant selectable marker comprises at least one natural or artificial intronic insertion region, and at least one gene product of interest is encoded by DNA located within at least one such intron. Such arrangements have the effect of increasing expression efficiency of the gene product of interest by, inter alia, decreasing the number of viable colonies obtained from an equivalent amount of plasmid DNA transfected per cell, while increasing the amount of gene product expressed in each clone.

For purpose of brevity and presentational efficiency, the focus of this section of the patent disclosure will be principally directed to a specific dominant selectable marker, neomycin phosphotransferase, which is incorporated into a mouse/human chimeric immunoglobulin expression vector. It is to be understood, however, that the invention disclosed herein is not intended, nor is it to be construed, as limited to these particular systems. To the contrary, the disclosed invention is applicable to mammalian expression systems in toto, where vector DNA is integrated into host cellular DNA.

One of the most preferred methods utilized by those in the art for producing a mammalian cell line that produces a high level of a protein (ie "production cell line") involves random integration of DNA coding for the desired gene product (ie "exogenous DNA") by using, most typically, a drug resistant gene, referred to as a "dominant selectable marker," that allows for selection of cells that have integrated the exogenous DNA. Stated again, those cells which properly incorporate the exogenous DNA including, eg, the drug resistant gene, will maintain resistance to the corresponding drug. This is most typically followed by co-amplification of the DNA encoding for the desired gene product in the transfected cell by amplifying an adjacent gene that also encodes for drug resistance ("amplification gene"), eg resistance to methotrexate (MTX) in the case of dehydrofolate reductase (DHFR) gene. The amplification gene can be the same as the dominant selectable marker gene, or it can be a separate gene. (As those in the art appreciate, "transfection" is typically utilized to describe the process or state of introduction of a plasmid into a mammalian host cell, while "transformation" is typically utilized to describe the process or state of introduction of a plasmid into a bacterial host cell).

Two amplification approaches are typically employed by those in the art. In the first, the entire population of transfected and drug resistant cells (each cell comprising at least one integration of the gene encoding for drug resistance) is amplified; in the second, individual clones derived from a single cell are amplified. Each approach has unique advantages.

With respect to the first approach, it is somewhat "easier" to amplify the entire population (typically referred to as a "shotgun" approach, an apt description) compared to individual clones. This is because amplification of individual clones initially involves, inter alia, screening of hundreds of isolated mammalian colonies (each derived from a single cell, most of which being single copy integrants of the expression plasmid) in an effort to isolate the one or two "grail" colonies which secrete the desired gene product at a "high" level, ie at a level which is (typically) three orders of magnitude higher than the lowest detectable expression level. These cells are also often found to have only a single copy integration of the expression plasmid. Additionally, amplifying individual clones results in production cell lines which contain fewer copies of the amplified gene as compared to amplification of all transfected cells (typically, 10–20 versus 500–1000).

With respect to the second approach, production cell lines derived from amplifying individual clones are typically derived in lower levels of the drug(s) used to select for those colonies which comprise the gene for drug(s) resistance nd the exogenous gene product (ie in the case of methotrexate and DHFR, 5 nM versus 1 $\mu$M). Furthermore, individual clones can typically be isolated in a shorter period of time (3–6 months versus 6–9 months).

Ideally then, the tangible benefits of both approaches should be merged: at a practical level, this would involve decreasing the number of colonies to be screened, and increasing the amount product secreted by these colonies. The resent invention accomplishes this task.

The position where the DNA of the dominant selectable marker of the plasmid DNA is integrated within the cellular DNA of the host cell determines the level of expression of the dominant selectable marker protein, as is recognized by those in the art. It is assumed that the expression of a gene encoding a protein of interest which is either co-linked to or positioned near the dominant selectable marker DNA is proportional to the expression of the dominant selectable marker protein. While not wishing to be bound by any particular theory, the inventor has postulated that if the gene used to select for the integration of the exogenous DNA in the mammalian cell (ie the dominant selectable marker) was designed such that translation of that dominant selectable marker was impaired, then only those plasmids which could overcome such impairment by over-production of the gene product of the dominant selectable marker would survive, eg, the drug-screening process. By associating the exogenous DNA with the dominant selectable marker, then, a fiorti, over-production of the gene product of the dominant selectable marker would also result in over-production of the gene product derived from the associated exogenous DNA. In accordance with this postulated approach, impairment of translation of the dominant selectable marker gene would be necessary, and an avenue for such impairment was the consensus Kozak portion of the gene.

By comparing several hundred vertebrate mRNAs, Marilyn Kozak in "Possible role of flanking nucleotides in recognition of the AUG initiator codon by eukaryotic ribosomes," *Nuc. Acids Res.* 9: 5233–5252 (1981) and "Compilation and analysis of sequences upstream from the translational start site in eukaryotic mRNAs" *Nuc. Acids Res.* 12: 857–872 (1984), proposed the following "consensus" sequence for initiation of translation in higher eukaryotes:

```
      -3       +1
      cc Acc AUG G
```

(As those in the art appreciate, uracil, U, replaces the deoxynucleotide thymine, T, in RNA.) In this sequence, referred to as a "consensus Kozak," the most highly conserved nucleotides are the purines, A and G, shown in capital letters above; mutational analysis confirmed that these two positions have the strongest influence on initiation. See, eg, Kozak, M. "Effects of intercistronic length on the efficiency of reinitiation of eukaryotic ribosomes." *Mol. Cell Bio.* 7/10: 3438–3445 (1987). Kozak further determined that alterations in the sequence upstream of the consensus Kozak can effect translation. For example, in "Influences of mRNA secondary structure on initiation by eukaryotic ribosomes." *PNAS* 83: 2850–2854 (1986) Kozak describes the "artificial" introduction of a secondary hairpin structure region upstream from the consensus Kozak in several plasmids that encoded preproinsulin; it was experimentally determined that a stable stem loop structure inhibited translation of the preproinsulin gene, reducing the yield of proinsulin by 85–95%.

Surprisingly, it was discovered by the inventor that by changing the purines A(-3 vis-a-vis ATG start codon) and G (+1) to pyrimidines, translation impairment was significant: when the consensus Kozak for the neomycin phosphotransferase gene was subjected to such alterations (as will be set forth in detail below), the number of G418 resistant colonies significantly decreased; however, there was a significant increase in the amount of gene product expressed by the individual G418 resistant clones. As those in the art will recognize, this has the effect of increasing the efficiency of the expression system-there are less colonies to screen, and most of the colonies that are viable produce significantly more product than would ordinarily be obtained. Confirmation of the inventor's postulated theory was thus experimentally determined.

As noted, for purposes of this patent document a, "consensus Kozak" comprises the following sequence:

```
  -3     +1
 Pxx ATG Pxx
``` a "partially impaired consensus Kozak" comprises the following sequence

```
    -3       +1
  P/Pyxx ATG P/Pyxx
``` and a disclosed and claimed "fully impaired consensus Kozak" comprises the following sequence:

```
  -3     +1
 Pyxx ATG Pyxx
``` where: "x" is a nucleotide selected from the group consisting of adenine (A), guanine (G), cytosine (C) or thymine (T) (uracil, U, in the case of RNA); "P" is a purine, ie A or G, "Py" is a pyridine, ie C or T/U; ATG is a conventional start codon which encodes for the amino acid methionine (Met); the numerical designations are relative to the ATG codon, ie a negative number indicates "upstream" of ATG and a positive number indicates "downstream" of ATG; and for the partially impaired consensus Kozak, the following proviso is applicable—only one of the −3 or +1 nucleotides is a pyridine, eg, if −3 is a pyridine, then +1 must be a purine or if −3 is a purine, then +1 must be a pyridine. Most preferably, the filly impaired consensus Kozak is associated with the site of translation initiation of a dominant selectable marker which is preferably (but not necessarily) co-linked to exogenous DNA which encodes for a gene product of interest. As used herein, "nucleotide" is meant to encompass natural and synthetic deoxy- and ribonucleotides as well as modified deoxy- and ribonucleotides, ie where the 3'OH, 5'OH, sugar and/or heterocyclic base are modified, as well as modification of the phosphate backbone, eg methyl phosphates, phosphorothioates and phosphoramidites.

Information regarding the gene sequence of the dominant selectable marker is preferably known; however, in lieu of the entire sequence, information regarding the nucleic acid sequence (or amino acid sequence) at the site of translation initiation of the dominant selectable marker must be known. Stated again, in order to effectuate a change in the consensus or partially impaired consensus Kozak, one must know the sequence thereof. Changing the consensus or partially impaired consensus Kozak to a fully impaired consensus Kozak sequence can be accomplished by a variety of approaches well known to those in the art including, but not limited to, site specific mutagenesis and mutation by primer-based amplification (eg PCR); most preferably, such change is accomplished via mutation by primer-based amplification. This preference is principally based upon the comparative "ease" in accomplishing the task, coupled with the efficacy associated therewith. For ease of presentation, a description of the most preferred means for accomplishing the change to a fully impaired consensus Kozak will be provided.

In essence, mutation by primer-based amplification relies upon the power of the amplification process itself—as PCR is routinely utilized, focus will be directed thereto. However, other primer-based amplification techniques (eg ligase chain reaction, etc.) are applicable. One of the two PCR primers ("mutational primer") incorporates a sequence which will ensure that the resulting amplified DNA product will incorporate the fully impaired consensus Kozak within the transcriptional cassette incorporating the dominant selectable marker of interest; the other PCR primer is complementary to another region of the dominant selectable marker; a transcriptional cassette incorporating the dominant selectable marker; or a vector which comprises the transcriptional cassette. By way of example, the complement to a dominant selectable marker which includes a consensus Kozak could have the following sequence (SEQ ID NO: 1):

```
3'-tagctaggTccTACCcc-5'
```

In order to create a fully impaired consensus Kozak, the mutational primer could have the following sequence (SEQ ID NO: 2) (for convenience, SEQ ID NO: 1 is placed over the mutational primer for comparative purposes):

```
5'-atcgatccTggATGCgg-3'
3'-tagctaggTccTACCcc-5'
          *       *
```

As is evident, complementarity is lacking in the primer (see, the "*" symbols). By utilizing excess mutational primer in the PCR reaction, when the sequence including the consensus Kozak is amplified, the resulting amplified DNA products will incorporate the mutations such that as the amplified DNA products are in turn amplified, the mutations will predominate such that a fully impaired consensus Kozak will be incorporated into the amplification product.

Two criteria are required for the mutational primer-first, the length thereof must be sufficient such that hybridization to the target will result. As will be appreciated, the mutational primer will not be 100% complementary to the target. Thus, a sufficient number of complementary bases are required in order to ensure the requisite hybridization. Preferably, the length of the mutational primer is between about 15 and about 60 nucleotides, more preferably between about 18 and about 40 nucleotides, although longer and shorter lengths are viable. (To the extent that the mutational primer is also utilized to incorporate an out-of-frame start codon or secondary structure, the length of the mutational primer can correspondingly increase). Second, the ratio of mutational primer to target must be sufficiently excessive to "force" the mutation. Preferably, the ratio of mutational primer to target is between about 250:1 to about 5000:1, more preferably between about 400:1 to about 2500:1, and most preferably between about 500:1 to about 1000:1.

Because the parameters of a PCR reaction are considered to be well within the level of skill of those in the art, details regarding the particulars of that reaction are not set forth herein; the skilled artisan is readily credited with recognizing the manner in which this type of mutation can be accomplished using PCR techniques—the foregoing is provided as a means of providing elucidation as opposed to detailed edification.

As noted, it is most preferred that the fully impaired consensus Kozak is associated with the site of translation initiation of a dominant selectable marker incorporated into a transcriptional cassette which forms a part of an expression vector. Preferred dominant selectable markers include, but are not limited to: herpes simplex virus thymidine kinase; adenosine deaminase; asparagine synthetase; Salmonella his D gene; xanthine guanine phosphoribosyl transferase ("XGPRT"); hygromycin B phosphotransferase; and neomycin phosphotransferase ("NEO"). Most preferably, the dominant selectable marker is NEO.

The dominant selectable marker herpes simplex virus thymidine kinase is reported as having the following partially impaired consensus Kozak:

```
 -3        +1
cg Cgt AGT Gct
```

See, Heller, S. "Insertional Activities of a Promotorless Thymidine Kinase Gene," *Mol. & Cell. Bio.* 8/8:3218–3302, FIG. 4, nucleotide 764. By changing the +1 purine (G) to a pyrimidine (C or T/U), a fully impaired Kozak as defined herein is generated (the −3 of the herpes simplex virus thymidine kinase is a pyrimidine). Changing +1 purine to a pyrimidine also has the effect of changing the encoded amino acid from alanine (GCT) to proline (CCT) or serine (TCT); it is preferred that conservative amino acid changes result from the changes to the nucleotides. Thus, it is preferred that the change to TCT be made because the change from alanine to serine is a more conservative amino acid change than changing alanine to proline.

Histidinol dehydrogenase is another dominant selectable marker. See, Hartmen, S. C. and Mulligan, R. C. "Two dominant acting selectable markers for gene transfer studies in mammalian cells," *PNAS* 85:8047–8051 (1988). The his D gene of Salmonella typhimunium has the following partially impaired consensus Kozak:

```
 -3        +1
gc Aga ATG Tta
```

As −3 is a purine, changing −3 to a pyrimidine (C or T/U) results in a fully impaired consensus Kozak; as is appreciated, because these nucleotides are upstream of the start codon, no impact on amino acid translation results from this change.

Hygromycin B phosphotransferase is another dominant selectable marker; the reported sequence for the hph gene (see, Gritz, L. and Davies, J. "Plasmid encoded hygromycin B resistance: the sequence of hygromycin B phosphotransferase gene and its expressing in *Escherichia coli* and *Succharomyces cerevisiae*" *Gene* 25:179–188, 1983) indicates that the consensus Kozak is:

```
 -3        +1
ga Gat ATG Aaa
```

Both −3 and +1 are purines: thus changing −3 and +1 to pyrimidines results in a fully impaired consensus Kozak (this results in the following encoded amino acids: +1 to C—glutamine; +1 to T—stop codon. Because this codon is downstream of the start codon, the change to the stop codon TAA should not be accomplished).

XGPRT is another dominant selectable marker. The reported partially impaired consensus Kozak of XGPRT has the following sequence:

```
 -3        +1
tt Cac ATG Agc
```

See, Mulligan, R. C. and Berg, P. "Factors governing the expression of a bacterial gene in mammalian cells." *Mol. & Cell Bio.* 1/5:449–459 (1981), FIG. 6. By changing the +1 purine to a pyrimidine, a fully impaired consensus Kozak is created; the effect on the encoded amino acid (AGC-serine) is as follows: CGC-arginine; TGC-cysteine.

Adenosine deaminase (ADA) can also be utilized as a dominant selectable marker. The reported consensus Kozak sequence for adenosine deaminase is:

```
 -3        +1
ga Acc ATG Gcc
```

See, Yeung, C. Y. et al., "Identification of functional murine adenosine deaminase cDNA clones by complementation in *Echerichia coli,*" *J. Bio. Chem.* 260/18:10299–10307 (1985), FIG. 3. By changing both −3 and +1 purines to pyrimidines, fully impaired consens Kozak sequences result. The encoded amino acid corresponding to GCC (alanine) is changed to either proline (CCC) or serine (TCC), with the change to serine being preferred, due to the conservative nature of this change.

The reported partially impaired consensus Kozak for asparagine synthetase is as follows:

```
 -3        +1
gc Acc ATG Tgt
```

See, Andrulis, I. L. et al., "Isolation of human cDNAs for asparagine synthetase and expression in Jensen rat sarcoma cells," *Mol. Cell. Bio.* 7/7:2435–2443 (1987). Changing the +3 purine to a pyrimidine results in a fully impaired consensus Kozak.

The partially impaired consensus Kozak for neomycin phosphotransferase (which includes an upstream out of frame start codon) is as follows:

```
              -3       +1
ggA TGg gga tcg ttt Cgc ATG Att
```

Changing the +1 purine to a pyrimidine has the effect of creating a fully impaired consensus Kozak (changes to the encoded amino acid isoleucine, ATT are as follows: CTT—leucine and TTT—phenylalanine, with the change to leucine being preferred, due to the conservative nature of this change).

The foregoing is not intended, nor is it to be construed as limiting; rather, in the context of the disclosed invention, the foregoing is presented in an effort to provide equivalent examples of changes in the reported consensus Kozak sequences or partially impaired consensus Kozak sequences of several well-known dominant selectable markers.

As noted, a most preferred dominant selectable marker is NEO. Particularly referred fully impaired consensus sequences for NEO are as follows:

```
Txx ATG Ctt                    (SEQ ID NO: 3)

Cxx ATG Ctt                    (SEQ ID NO: 4)

Txx ATG Ttt                    (SEQ ID NO: 5)

Cxx ATG Ttt                    (SEQ ID NO: 6)
``` where x are nucleotides. SEQ. ID. NO. 3 is most preferred; and xx are preferably CC.

Other transcriptional cassettes, which may or may not include a fully impaired consensus Kozak, can be incorporated into a vector which includes transcriptional cassettes containing the disclosed and claimed fully impaired consensus Kozak; such "other transcriptional cassettes" typically are utilized to allow for "enhancement," "amplification" or "regulation" of gene product repression. For example, co-transfection of the exogenous DNA with the dehydrofolate reductase (DHFR) gene is exemplary. By increasing the levels the antifolate drug methotrexate (MTX), a competitive inhibitor of DHFR, presented to such cells, an increase in DHFR production can occur via amplification of the DHFR gene. Beneficially, extensive amounts of flanking exogenous DNA will also become amplified; therefore, exogenous DNA inserted co-linear with an expressible DHFR gene will also become overexpressed. Additionally, transcriptional cassettes which allow for regulation of expression are available. For example, temperature sensitive COS cells, derived by placing SV40ts mutant large T antigen gene under the direction of Rous sarcoma virus LTR (insensitive to feedback repression by T antigen), has been described. See, 227 *Science* 23–28 (1985). These cells support replication from SV40 ori at 33° C. but not at 40° C. and allow regulation of the copy number of transfected SV40 ori-containing vectors. The foregoing is not intended, nor is it to be construed, as limiting; rather the foregoing is intended to be exemplary of the types of cassettes which can be incorporated into expression vectors comprising the disclosed fully impaired consensus Kozak. The skilled artisan is credited with the ability to determine the specific type of other transcriptional cassettes, vis-a-vis the objective of the expression system, which are applicable and which can be advantageously exploited.

As indicated above, in particularly preferred embodiments of the invention, at least one out-of-frame start codon (ie ATG) is located upstream of the fully impaired consensus Kozak start codon, without a stop codon being located between the out-of-frame start codon and the fully impaired consensus Kozak start codon. The intent of the out-of-frame start codon is to, in effect, further impair translation of the dominant selectable marker.

As used herein, the term "stop codon" is meant to indicate a "nonsense codon," ie a codon which does not encode one of the 20 naturally occurring amino acids such that translation of the encoded material terminates at the region of the stop codon. This definition includes, in particular, the traditional stop codons TAA, TAG and TGA.

As used herein, the term "out-of-frame" is relative to the fully impaired consensus Kozak start codon. As those in the art appreciate, in any DNA macromolecule (or RNA macromolecule) for every in-frame sequence, there are two out-of-frame sequences. Thus, for example, with respect to the following sequence incorporating a fully impaired consensus Kozak:

```
              -3       +1
gcA TGc cAT Ggc Cxx ATG Cxx
``` the in-frame codons are separated by triplets, eg, gcA, TGc, cAT and Ggc; the out-of-frame codons would include, eg cAT, ATG, Gcc, ccA, ATG and TGg. Thus, two start codons (in capital letters and underlined) are out-of-frame relative to the start codon of the fully impaired consensus Kozak.

When such an out-f-frame start codon is utilized, it is preferred that this be within about 1000 nucleotides upstream of the fully impaired consensus Kozak start codon, more preferably within about 350 nucleotides upstream of the fully impaired consensus Kozak start codon, and most preferably within about 50 nucleotides of the fully impaired consensus Kozak start codon.

As is appreciated, the upstream sequence can be manipulated to achieve positioning at least one out-of-frame sequence upstream of the fully impaired consensus Kozak start codon using (most preferably) a mutational primer used in the type of amplification protocol described above.

Utilization of a fully impaired consensus Kozak start codon located within a secondary structure (ie a "stem-loop" or "hairpin") is beneficially viable to impairment of translation of the protein encoded by the dominant selectable marker. In such an embodiment, it is preferred that this start codon be located within the stem of a stem loop secondary structure. These, by way of schematic example, in such an embodiment, the start codon of the fully impaired consensus Kozak is positioned as follows:

```
         T
       x   x
       x x
       x A
       x T
       x G
    xA TGxx Cxx
```

(An out-of-frame start codon which is not part of the secondary structure is also represented.) As is appreciated, within the stem loop, complementarity along the stem is, by definition, typically required. For exemplary methodologies regarding, inter alia, introduction of such secondary structures into the sequence, as well as information regarding secondary structure stability, see, Kozak, PNAS, 1986, supra.

As noted, it is preferred that a dominant selectable market with a naturally occurring intronic insertion region or an artificially created intronic insertion region be utilized and at least one gene product of interest inserted within this region. While not wishing to be bond by any particular theory, the inventor postulates that such an arrangement increases expression efficiency because the number of viable colonies that survive the selection process via-a-vis the dominant selectable marker will decrease; the colonies that do survive the selection process will, by definition, have expressed the protein necessary for survival, and in conjunction therewith, the gene product of interest will have a greater tendency to be expressed. As further postulated, the RNA being transcribed from the gene product of interest within the intronic insertion region interferes with completion of transcription (elongation of RNA) of the dominant selectable marker; therefore, the position that the dominant selectable marker is integrated within the cellular DNA is likely to be a position where a larger amount of RNA is initially transcribed.

As is appreciated, prokaryotic proteins do not typically include splices and introns. However, the majority of dominant selectable markers which are preferred for expression vector technology are derived from prokaryotic systems. Thus, when prokaryotic-derived dominant selectable markers are utilized, as is preferred, it is often necessary to generate an artificial splice within the gene so to create a location for insertion of an intron comprising the gene product of interest. It is noted that while the following rules are provided for selection of a splice site in prokaryotic genes, they can be readily applied to eukaryotic genes. A general mechanism for the splicing of messenger RNA precursors in eukaryotic cells is delineated and summarized in Sharp, Philip A. "Splicing of Messenger RNA Precursors" *Science*, 235: 736–771 (1987) (see, in particular, FIG. 1) which is incorporated herein by reference. Based upon Sharp, there are four minimum criteria in the nucleic acid sequence which are necessary for a splice: (a) 5' splice donor; (b) 3' splice acceptor, (c) branch point, and (d) polypyrimidine tract. The consensus sequences for the 5' splice donor is reported to be

```
  C    A
AAG/GTGAGT
``` and for the 3' splice acceptor, NCAG/G (where a "/" symbol indicates the splice site); see, Mount, S. M. "A Catalogue of Splice Junction Sequences" *Nuc. Acids. Res.* 10/2:459–472 (1992) which is incorporated herein by reference. The consensus sequence for the branch point, ie. the location of the lariat formation with the 5' splice donor, is reported as PyNPyPAPy; and the reported preferred branch site for mammalian RNA splicing is TACTAAC (Zhuang, Y. et al. "UACUAAC is the preferred branch site for mammalian mRNA splicing" *PNAS* 86: 2752–2756 (1989), incorporated herein by reference). Typically, the branch point is located at least approximately 70 to about 80 base-pairs from the 5'-splice donor (there is no defined upper limit to this distance). The poly pyrimidine tract typically is from about 15 to about 30 base pairs and is most typically bounded by the branch point and the 3' splice acceptor.

The foregoing is descriptive of the criteria imposed by nature on naturally occurring splicing mechanisms. Because there is no exact upper limit on the number of base pairs between the 5' splice donor and the branch point, it is preferred that the gene product of interest be inserted within this region in situations where a natural intron exists within the dominant selectable marker. However, as noted, such introns do not exist within most of the preferred dominant selectable markers; as such, utilization of artificial introns are preferably utilized with these markers.

In order to generate an artificial intron, a "splice donor-:splice acceptor" site must be located within the encoding region of the dominant selectable marker. Based upon Sharp and Mount, it is most preferred that the following sequence function as the splice donor:splice acceptor site—CAGG (with the artificial splice occurring at the GG region). A preferred sequence is AAGG.

Focusing in on the most preferred sequence CAGG, the following codons and amino acids can be located within the encoding region of the dominant selectable marker for generation of the artificial intronoc insertion region:

| A | | B | | C | |
|---|---|---|---|---|---|
| CAG/ | GNN | NCA | G/GN | NNC | AG/G |
| Gln | Ala | Ala | Gly | Ala Leu | Arg |
|  | Asp | Pro |  | Arg Phe |  |
|  | Gly | Ser |  | Asn Pro |  |
|  | Glu | Thr |  | Asp Ser |  |
|  | Val |  |  | Cys Thr |  |
|  |  |  |  | Gly Tyr |  |
|  |  |  |  | His Val |  |
|  |  |  |  | Ile |  |

(As will be appreciated, the same approach to determining viable amino acid residues can be utilized for the preferred sequence of AAGG). The most preferred codon group for derivation of the splice donor:splice acceptor site is group A. Once these amino acid sequences are located, a viable point for generation of an artificial intronic insertion region can be defined.

Focusing on the preferrred NEO dominant selectable marker, amino acid residues Gln Asp (codon group A) are located at the positions 51 and 52 of NEO and amino acid residues Ala Arg (codon group C) are located at positions 172 and 173 (as is appreciated, multiple artificial intronic insertion regions may be utilized). Focusing on residues 50–53 of NEO, the nucleic acid and amino acid sequences are as follows:

```
     50  51  52  53
5' CTG CAG GAC GAG 3'
   Leu Gln Asp Glu
```

Accordingly, an artificial intronic insertion region can be generated between residues 51 and 52 of NEO. This region more preferably comprises a branch point, a polyprimidine tract and, preferably, a region for insertion of a gene product of interest, ie a region amendable to enzymatic digestion.

Two criteria are import for the artificial intronic insertion region: the first two nucleic acid residues of the 5' splice site (eg abutting CAG) are most preferably GT and the first two nucleic acid residues of the 3' splice site (eg abutting G) are most preferably AG.

Using the criteria defined abouve, an artificial intronic insertion region was between amino acid residues 51 and 52 of NEO:

```
       50 NEO 51                                                           52 NEO 53
       LEU GLN                    Branch         Polypyrimide Tract   ASP    GLU 3'
  5' CTG CAG/GTAAGT GCGGCCGC TACTAAC(TC)3CT(C)3TCC(T)5 C CTGCAG/GAC   GAG
                    Not I
```

(Details regarding the methology for creating this artificial intronic insertion region are set forth in the Example Section to follow). The Not I site was created as the region where the gene product of interest can be incorporated. Therefore, upon incorporation, the gene product of interest is located between amino acid residues 51 and 52 of NEO, such that during NEO transmission, the gene product of interest will be "spliced-out".

The host cell line is most preferably of mammalian origin; those skilled in the art are credited with ability to preferentially determine particular host cell lines which are best suited for the desired gene product to be expressed therein. Exemplary host cell lines include, but are not limited to, DG44 and DXBII carcinoma), CV1 (monkey kidney line), COS (a derivative of CV1 with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-lclBPT (bovine endothelial cells), RAJI (human lymphocyte) and 293 (human kidney). Host cell lines are typically available from commercial services, the American Tissue Culture Collection or from published literature.

Preferably the host cell line is either DG44 or SP2/O. See, Urland, G. et al., "Effect of gamma rays and the dihydrofolate reductase locus: deletions and inversions." *Som. Cell & Mol. Gen.* 12/6:555–566 (1986) and Shulman, M. et al., "A better cell line for making hybridomas secreting specific antibodies." *Nature* 276:269 (1978), respectively. Most preferably, the host cell line is DG44. Transfection of the plasmid into the host cell can be accomplished by any technique available to those in the art. These include, but are not limited to, transfection (including electrophoresis and electroporation), cell fusion with enveloped DNA, microinjection, and infection with intact virus. See, Ridgway, A. A. G. "Mammalian Expression Vectors." Chapter 24.2, pp. 470–472 *Vectors,* Rodriguez and Denhardt, Eds. (Butterworths, Boston, Mass. 1988). Most preferably, plasmid introduction into the host is via electroporation.

EXAMPLES

The following examples are not intended, nor are they to be construed, as limiting the invention; the examples are intended to demonstrate the applicability of an embodiment of the invention disclosure herein. The disclosed fully impaired consensus Kozak sequence is intended to be broadly applied as delineated above. However, for presentational efficiency, exemplary uses of particularly preferred embodiments of fully impaired consensus Kozak sequences are utilized in conjunction with tandem chimeric antibody expression vectors (also referred to herein as antibody expression vectors) as disclosed below.

I. Tandem Chimeric Antibody Expression ("TCAE") Vector

B cell lymphocytes arise from pluripotent stem cells and proceed through ontogeny to fully matured antibody secreting plasma cells. The human B lymphocyte-restricted differentiation antigen Bp35, referred to in the art as "CD20," is a cell surface non-glycosylated phosphoprotein of 35,000 Daltons; CD20 is expressed during early pre-B cell development just prior to the expression of cytoplasmic $\mu$ heavy chains. CD20 is expressed consistently until the plasma cell differentiation stage. The CD20 molecule regulates a step in the activation process which is required for cell cycle initiation and differentiation. Because CD20 is expressed on neoplastic B cells, CD20 provides a promising target for therapy of B cell lymphomas and leukemias. The CD20 antigen is especially suitable as a target for anti-CD20 antibody mediated therapy because of accessibility and sensitivity of hematopoietic tumors to lysis via immune effector mechanisms. Anti-CD20 antibody mediated therapy, inter alia, is disclosed in co-pending Ser. No. 07/978,891 and Ser. No. 08/149,099, filed simultaneously herewith. The antibodies utilized are mouse/human chimeric anti-CD20 antibodies expressed at high levels in mammalian cells (chimeric anti-CD20"). This antibody was derived using vectors disclosed herein, to wit: TCAE 5.2; ANEX 1; ANEX 2; GKNEOSPLA3F; and NEOSPLA3F (an additional vector, TCAE 8, was also utilized to derive chimeric anti-CD20 antibody—TCAE 8 is identical to TCAE 5.2 except that the NEO translational start site is a partially impaired consensus Kozak. TCAE 8 is described in the co-pending patent document filed herewith.).

Figure 6:
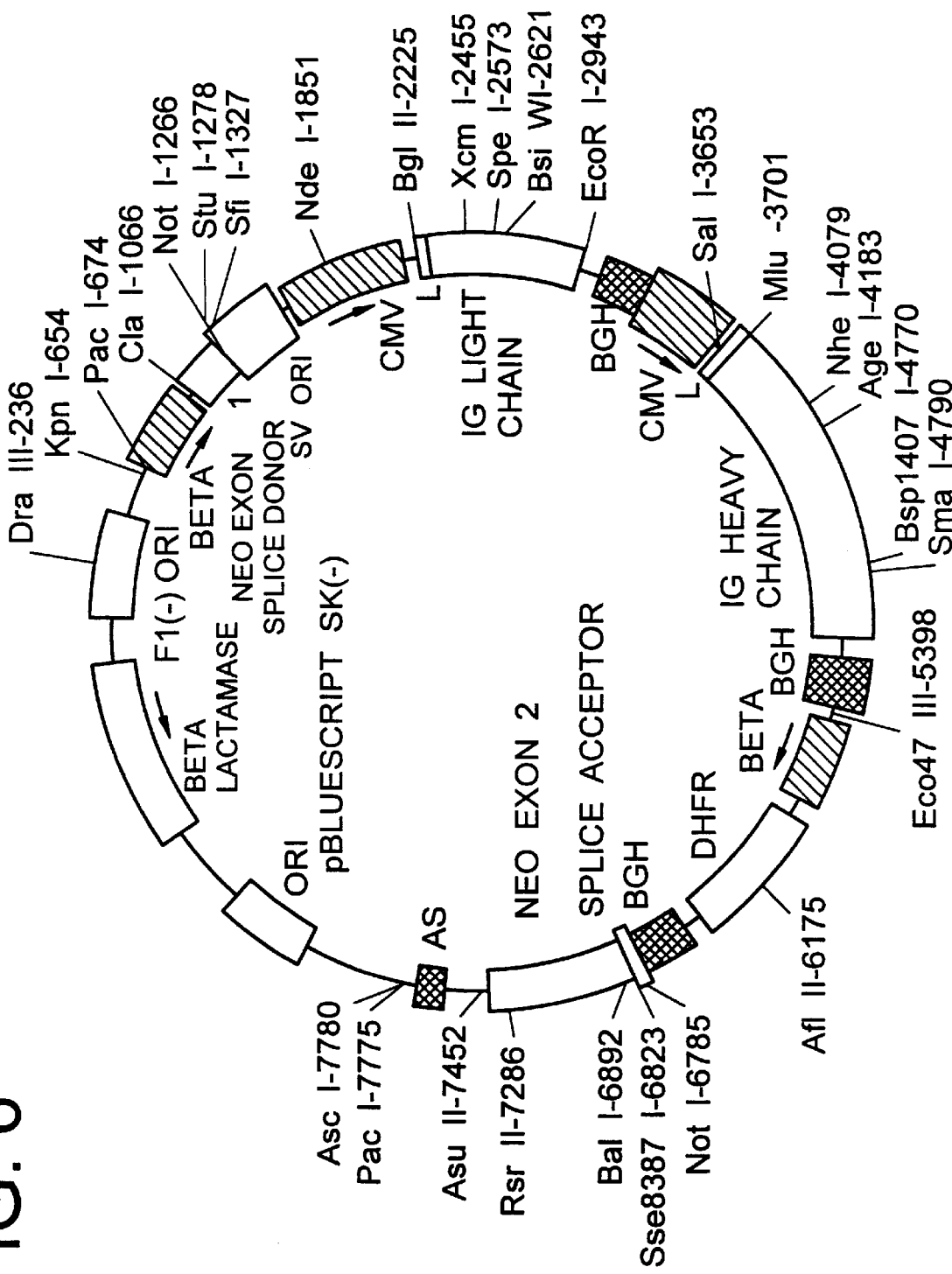
FIG. 6 provides a diagrammatic representation of a NEOSPLA vector designed for expression of mouse/human chimeric immunoglobulin.

In commonly-assigned U.S. Ser. No. 07/912,292, disclosed, inter alia, are human/Old World monkey chimeric antibodies; an embodiment of the invention disclosed therein are human/macaque chimeric anti-CD4 antibodies in vector TCAE 6 (see, FIG. 6 of Ser. No. 07/912,292, and corresponding discussion). TCAE 6 is substantially identical to TCAE, 5,2; TCAE 6 contains human lambda constant region, while TCAE 5.2 contains human kappa constant region. TCAE 5.2 and ANEX 1 (referred to in that patent document as TCAE 12) are disclosed as vectors which can be utilized in conjunction with human/Old World monkey chimeric antibodies. The comparative data set forth in Ser. No. 07/912,292 vis-a-vis TCAE 5.2 and ANEX 1 is relative to expression of chimeric anti-CD20 antibody.

TCAE 5.2 was derived from the vector CLDN, a derivative of the vector RLDN10b (see, 253 *Science* 77–91, 1991). RLDN10b is a derivative of the vector TND (see, 7DNA 651–661, 1988). le the vector "family line" is as follows: TDN→RLDN10b→CLDN→TCAE 5.2→ANEX 1 (the use of the "→" symbol is not intended, nor is it to be construed, as an indication of the effort necessary to achieve the changes from one vector to the next; e.g. to the contrary, the number and complexity of the steps necessary to generate TCAE 5.2 from CLDN were extensive).

TND was designed for high level expressions of human tissue plasminogen activator. RLDN10b differs from TND in the following ways: the dihydrofolate reductase ("DHFR") transcriptional cassette (comprising promoter, murine DHFR cDNA, and polyadenylation region) was placed in between the tissue plasminogen activator cassette ("t-PA expression cassette") and the neomycin phosphotransferase ("NEO" cassette") so that all three cassettes were in tandem and in the same transcriptional orientation. The TND vector permitted selection with G418 for cells carrying the DHFR, NEO and t-PA genes prior to selection for DHFR gene amplification in response to methotrexate, MTX. The promoter in front of the DHFR gene was changed to the mouse beta globin major promoter (see, 3 *Mol. Cell Bio.* 1246–1254, 1983). Finally, the t-PA CDNA was replaced by a polylinker such that different genes of interest can be inserted in the polylinker. All three eukaryotic transcriptional cassettes (t-PA, DHFR, NEO) of the TND vector can be separated from the bacterial plasmid DNA (pUC19 derivative) by digestion with the restriction endonuclease Not I.

CLDN differs from RLDN10b in the following ways: The Rous LTR, positioned in front of the polylinker, was replaced by the human cytomegalovirus immediate early gene promoter enhancer ("CMV"), (see, 41 *Cell* 521, 1985), from the Spe I site at −581 to the Sst I site at −16 (these numbers are from the Cell reference).

As the name indicates, TCAE vectors were designed for high level expressions of chimeric antibody. TCAE 5.2 differs from CLDN in the following ways:

A. TCAE 5.2 comprises four (4) transcriptional cassettes, as opposed to three (3), and these are in tandem order, ie a human immunoglobulin light chain absent a variable region; a human immunoglobulin heavy chain absent a variable region; DHFR; and NEO. Each transcriptional cassette contains its own eukaryotic promoter and polyadenylatin region (reference is made to FIG. 2 which is a diagrammatic representation of the TCAE 5.2 vector). The CMV promoter/enhancer in front of the immunoglobulin heavy chain is a truncated version of the promoter/enhancer in front of the light chain, from the Nhe I site at −350 to the Sst I site at −16 (the numbers are from the Cell reference, supra). Specifically, 1) A human immunoglobulin light chain constant region was derived via amplification of cDNA by a PCR reaction. In TCAE 5.2, this was the human immunoglobulin light chain kappa constant region (Kabat numbering, amino acids 108–214, allotype Km 3), and the human immunoglobulin heavy chain gamma 1 constant region (Kabat numbering amino acids 114–478, allotype Gmla, Gmlz). The light chain was isolated from normal human blood (IDEC Pharmaceuticals Corporation, La Jolla, Calif.); RA therefrom was used to synthesize cDNA which was then amplified using PCR techniques (primers were derived vis-a-vis the consensus Kabat). The heavy chain was isolated (using PCR techniques) from cDNA prepared from RNA which was in turn derived from cells transfected with a human IgG1 vector (see, 3 Prot. Eng. 531, 1990; vector $pN_{\gamma 1}62$). Two amino acids were changed in the isolated human IgG1 to match the consensus amino acid sequence in Kabat, to wit: amino acid 225 was changed from valine to alanine (GTT to GCA), and amino acid 287 was changed from methionine to lysine (ATG to AAG);

2) The human immunoglobulin light and heavy chain cassettes contain synthetic signal sequences for secretion of the immunoglobulin chains;

3) The human immunoglobulin light and heavy chain cassettes contain specific DNA restriction sites which allow for insertion of light and heavy immunoglobulin variable regions which maintain the transitional reading frame and do not alter the amino acids normally found in immunoglobulin chains;

4) The DHFR cassette contained its own eukaryotic promoter (mouse beta globin major promoter, "BETA") and polyadenylation region (bovine growth hormone polyadenylation, "BGH"); and 5) The NEO cassette contained its own eukaryotic promoter (BETA) and polyadenylation region (SV40 early polyadenylation, "SV").

With respect to the TCAE 5.2 and the NEO cassette, the Kozak region was a consensus Kozak (which included an upstream Cla I site SEQ D NO: 7):

```
         ClaI       -3   +1
TTGGGAGCTTGG ATCGAT ccAcc ATG Gtt
```

ANEX 1 (previously named TCAE 12 in the referenced case) is identical to TCAE 5.2 except that in the NEO cassette, the Kozak region was fully impaired (SEQ ID NO: 8):

```
         ClaI       -3   +1
TTGGGAGCTTGG ATCGAT ccTcc ATG Ctt
```

Figure 3:
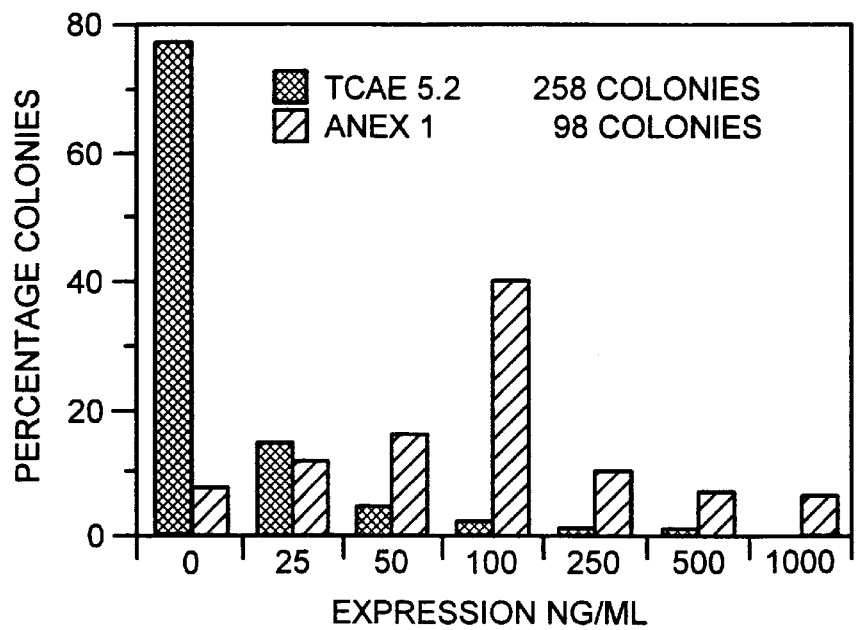
FIG. 3 is a histogram comparing protein expression levels with the vectors TCAE 5.2 and ANEX 1.
Figure 5:
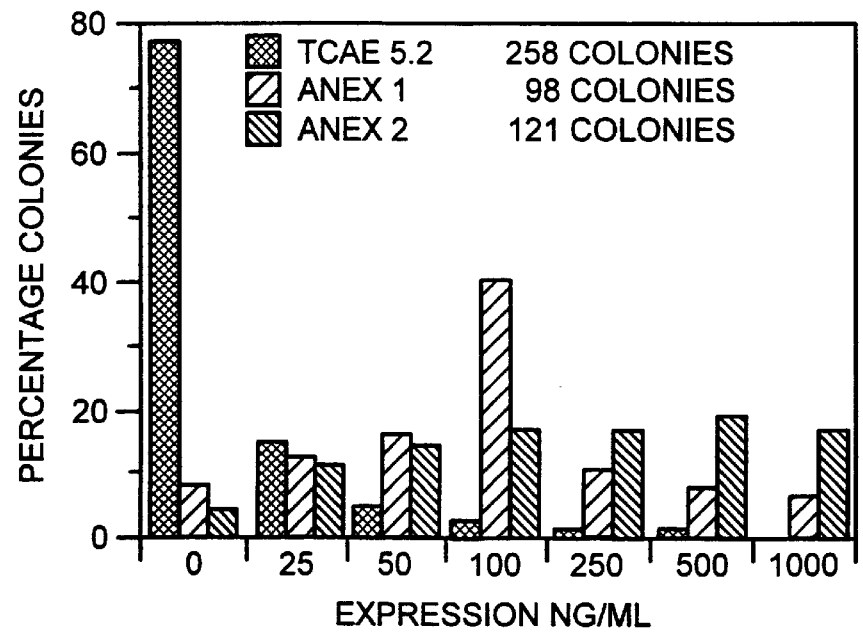
FIG. 5 is a histogram comparing protein expression levels with the vectors TCAE 5.2, ANEX 1 and ANEX 2.

As disclosed in the commonly-assigned referenced case, the impact of utilization of the fully impaired consensus Kozak was striking: relative to TCAE 5.2, there was a significant (8-fold) reduction in the number of ANEX 1 G418 resistant colonies (258 from two electroporations versus 98 from six electroporations) from the same amount of plasmid DNA transfected per cell; and, there was a significant increase in the amount of co-linked gene product expressed in each of the ANEX 1 clones. Referencing the histogram of FIG. 3 (FIG. 16 of the commonly assigned referenced case), 258 colonies were derived from 2 electroporations of 25 µg of DNA containing a neomycin phosphotransferase gene with a consensus Kozak at the translation start site. Two-hundred and one (201) of these colonies did not express any detectable gene product (less than 25 ng/l of chimeric immunoglobulin), and only 8 colonies expressed more than 100 ng/ml. Again, referencing FIG. 3, 98 colonies were derived from 6 electroporations for ANEX 1 of 25 µg of DNA containing a neomycin phosphotransferase gene with the fully impaired consensus Kozak at the translation start site (6 electroporations were utilized in order to generate statistically comparative values; this was because on average, each electroporation for ANEX 1 yielded about 16 colonies, as opposed to about 129 colonies per electroporation for TCAE 5.2). Eight (8) of the ANEX 1 colonies did not express any detectable gene product (less than 25 ng/ml), while 62 of these colonies were expressing greater than 100 ng/ml; of these 62 colonies, nearly 23 were expressing over 250 ng/ml (23%), with 6 expressing greater than 1000 ng/ml (6%).

The foregoing evidences, inter alia, the following: 1) because the difference between TCAE 5.2 and ANEX 1 was limited to the Kozak translation start site of the NEO gene, and because the gene product of interest (chimeric anti-CD20 antibody) was co-linked to the NEO gene, a conclusion to be drawn is that these differences in results are attributed solely to the differences in the Kozak translation start site; 2) it was experimentally confirmed that utilization of a fully impaired consensus Kozak in conjunction with a dominant selectable number resulted in significantly less viable colonies; 3) it was experimentally confirmed that utilization of a fully impaired consensus Kozak in conjunction with a dominant selectable marker co-linked to a desired gene product significantly increased the amount of expressed gene product. Thus, the number of colonies to be screened decreased while the amount of expressed gene product increased.

II. Impact of Out-of-Frame Start Sequence

Conceptually, further impairment of translation initiation of the dominant selectable marker of ANEX 1 could be effectuated by utilization of at least one out-of-frame ATG start codon upstream of the neomycin phosphotransferase start codon. Taking this approach one step further, utilization of a secondary structure ("hairpin") which incorporated the neo start codon within the stem thereof, would be presumed to further inhibit translation initiation. Thus, when the out-of-frame start codon/fully impaired consensus Kozak was considered, this region was designed such that the possibility of such secondary structures was increased.

As indicated previously, the Kozak region for the neo start codon in the ANEX 1 vector is:

```
TTGGGAGCTTGG ATCGAT CC Tcc ATG Ctt
```

The desired sequence for a vector identical to ANEX 1 but incorporating the above-identified changes vis-a-vis the neo start codon, referred to as ANEX 2, is as follows (SEQ ID NO: 9):

```
CCA GCA TGG AGG A ATCGAT CC Tcc ATG Ctt
```

(The out-of-frame start codon is underlined.) The fully impaired consensus Kozak of ANEX 2 is identical to that of ANEX 1. The principal difference is the inclusion of the upstream out-of-frame start codon. A possible difference is the formation of a secondary structure involving this sequence, proposed as follows:

```
CG  }
T A } CLA I site
A T }
 AT
 GC
 GC
 AT
 GC
 GC
 TA
 AT
 CG
 GC
 AT
 CT
 CG
```

The sequence in bold, ATG, is the upstream out-of-frame start codon; the "loop" portion of the secondary structure is the CLA I site; and the sequence between the "T" and "C" (italics and bold) is the start codon (underlined) of the fully impaired consensus Kozak.

Figure 4:
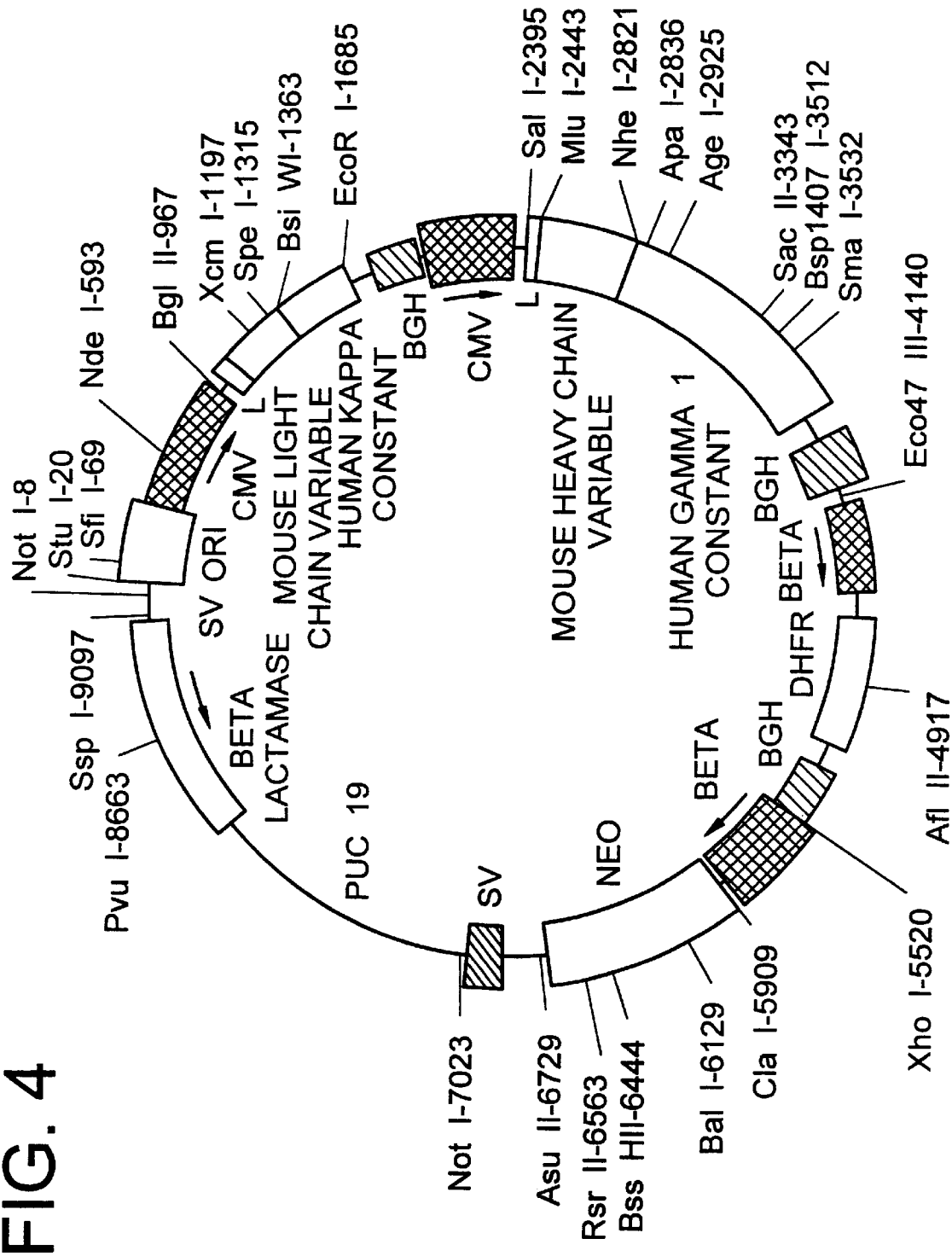
FIG. 4 provides a diagrammatic representation of the vector ANEX 2 designed for expression of mouse/human chimeric immunoglobulin, where the immunoglobulin genes are arranges in a tandem configuration using neomycin phosphotransferase as the dominant selectable marker.

In order to effectuate this change, a PCR fragment was cloned into anti-CD20 in AMEX 1 from Xho I (5520) to Cla 1 (5901); see, FIG. 4. Primers were as follows:
3'-Primer 489 (SEQ ID NO: 10):

```
5'-GGA GGA TCG ATT CCT CCA TGC TGG
   CAC AAC TAT GTC AGA AGC AAA TGT
   GAG C-3'
```

The upper-lined portion of Primer 489 is a Cla I site; the under-lined portion is the fully impaired consensus Kozak translation start site.
5'-Primer 488 (SEQ. ID. NO. 11):

```
5'-CTG GGG CTC GAG CTT TGC-3'
```

The upper-lined portion of Primer 485 is an Xho I site.

These primers were prepared using an ABI 391 PCR MATE™ DNA synthesizer (Applied Biosystems, Foster City, Calif.). Phosphoramidites were obtained from Cruachem (Glasgow, Scotland): IA(bz)—Prod. No. 20-8120-21; dG(ibu)—Prod. No. 20-8110-21; dC(bz)—Prod. No. 20-8130-21; T—Prod. No. 20-8100-21.

Conditions for the PCR reaction using these primers were as follows: 2λ ("microliters") of anti-CD20 in TCAE 5.2 in plasmid grown in $E.\ coli$ strain GM48 (obtained from the ATCC) was admixed with 77λ of deionized water; 2λ of Primer 488 (64 pmoles); and 4λ of primer 489 (56 pmoles). This was followed by a denaturation step (94° C., 5 min.) and a renaturation step (54° C., 5 min.).

Thereafter, 4λ of 5 mn dNTPS (Promega, Madison, Wis.: dATP, Prod. No. U1201; dCTP, Prod. No. U1221; dGTP, Prod. No. U1211; dThp, Prod. No. U1231), 1 of Pfu DNA polymerase (Stratagene, La Jolla, Calif. Prod. No. 600135, 2.5 U/ml), and 50% of mineral oil overlay was added thereto, followed by 30 cycles, with each cycle comprising the following: 72° C., 2 min.; 94° C., 1 min.; 54° C., 1 min. Ten microliters (10λ) of this admixture was analyzed by agarose gel electrophoresis (results not shown); a single band was found at about 400 base pairs.

The PCR product and the vector were prepared for ligation as follows: Anti-CD2(3 in ANEX 1 plasmid grown in $E.\ coli$ bacterial strain GM48 was digested with Cla 1 and Xho 1 as follows: 20 of anti-CD20 in ANEX 1 was admixed with 10λ of 10XNEB4 buffer (New England Biolabs, Beverly, Mass.; hereinafter, NEB); 5λ Cla 1 (NEB, Prod. No. 197 S, 60u); and 64) deionized water. This admixture incubated overnight at 37° C., followed by the addition of 5λ Xho 1 (NEB, Prod. No. 146 S, 100 u) and incubation at 37° C. for 2 hrs. The resulting material is designated herein as "Cla 1/Xho 1 cut ANEX 1". The approximate 400 base pair PCR fragment was prepared and digested with Cla 1 and Xho 1 as follows: 90 of the PCR fragment was admixed with 10λ of 3M NaOAc; 1λ 10% sodium dodecyl sulfate (SDS); and 90% phenyl/CHCl₃/isoamyl. This admixture was vortexed for sec. followed by a 1 min. spin (1700 RPM). The aqueous phase was subjected to a spin column which resulted in 85λ total admixture. To this admixture was added 10% 10XNEB4, 1λ bovine serum albumin (BSA,100x; NEB), 2λ Cla 1 (24 u), and 2) Xho 1 (40 u). This admixture was incubated at 37° C. for 2 hrs. The resulting material is designated herein as "Cla 1/Xho 1 cut PCR 488/489". Both Cla 1/Xho 1 cut ANEX 1 and Cla 1/Xho 1 cut PCR 488/489 were analyzed by agarose gel electrophoresis and the resulting bands were observed at the same relative location on the gel (results not shown). Ligation of Cla 1/Xho 1 cut PCR 488/489 and Cla 1/Xho 1 cut ANEX 1 was accomplished as follows: 1λ of tRNA (Sigma, St. Louis, Mo., Prod. No. R-8508) was admixed with 1λ 10% SDS; 10% 3M NaOAc; 45λ of Cla 1/Xho 1 cut PCR 488/489 (about 22.5 ng); a 1:4 dilution (0.25λ) of Cla 1/Xho 1 cut ANEX 1 (about 32 ng) in 0.75λ tris-hydroxymethyl aminomethane ethylenediamine tetracetic acid (TE); and 42λ TE. To this admixture was added 90λ phenyVCHCl₃/isoamyl, followed by a 30 sec. vortex and a 1 min. spin (1700 RPM). The aqueous phase was transferred to a new tube, followed by addition of 270λ of 100% EtOH (−20° C), 10 min. spin (12,000 RPM) followed by addition of another 270λ of 100% EtOH (−20° C.) and another 1 min. spin (13,000 RPM). This admixture was dried in a SpeedVAC™ and resuspended in 17λ TE 2λ ligase buffer (Promega, T4 DNA Ligase kit, Prod. No. M180) and 1λ ligase (Promega Ligase kit). This ligation mix incubated at 14° C. overnight. Twenty microliters (20X) of the ligation mix was admixed with 10λ 3M NaOAc, 1λ 10% SDS, 69λ TE, and 90λ phenyl/CHCl₃/isoamyl. This admixture was vortexed for 30 sec., followed by a 1 min. spin (1700 RPM). The aqueous phase was transferred to a new tube and 270% of 100% EtOH (−20° C.) was added thereto, followed by a 10 min. spin (1700 RPM). This admixture was dried in a SpeedVAC™ and resuspended in 20% TE. Ten microliters of the resuspended admixture was transformed in $E.\ coli$ X-L1 blue™ (Stratagene, La Jolla, Calif.), following manufacturer instructions. Ten (10) bacterial colonies were inoculated in LB Broth (Gibco BRL, Grand Island, N.Y., Prod. No. M27950B) including ampicillin (50 μg/ml; Sigma, Prod. No. A-9393). Plasmids were isolated from the 10 cultures with a Promega DNA purification System (Prod. No. PR-A7100), following manufacturer instructions; these plasmids may have comprised the ANEX 2 vector, depending on the sufficiency of the foregoing.

ANEX 2 includes a Hinf I site ("GAATC") upstream of the neo start site (−9 to −13 relative to the neo start codon); ANEX 1 does not include this Hinf I site. The purified plasmids comprising putative ANEX 2, and previously purified ANEX 1 standard, were subjected to Hinf 1 digestion as follows: 2) of each isolate was admixed with 8λ of Hinf I digestion buffer (15λ 10x NEB2 buffer; 15λ Hinf I (NEB, Prod. No. 155S, 10 u/λ); and 90λ H₂O). This admixture incubated for 3 hrs. at 37° C. and each isolate was analyzed via agarose gel electrophoresis (results not shown);

nine (9) of the bands were substantially identical to the ANEX 1 standard, one(1) showed a slight difference in band pattern. For this single isolate, the first two bands were at 1691 and 670 kB; for the ANEX 1 Hinf I digested product, the first three bands were at 1691, 766, and 670 kB. The missing band at 766 kB for the single isolate was attributed to the presence of the Hinf I site therein, indicating that the desired change to ANEX 1 was incorporated into this vector. This vector was designated "Anti-CD20 in ANEX 2 (G1, K)," and is generally referred to by the inventor as ANEX 2.

Electroporation of anti-CD20 in ANEX 2 was accomplished as follows: two-hundred and forty microliters (240λ) of the anti-CD20 in ANEX 2 DNA (400 μg) was admixed with 100λ of 10× NEB2 buffer; 100λ of Stu I (NEB, Prod. No. 187S, 1000 u); and 560λ TE, and incubated at 37° C. for 2hrs. This admixture was then placed over 8 spin columns (125w each), followed by addition of 110λ 10× Not I buffer (NEB); 10λ 100× BSA; and 20 of Not I (NEB, Prod. No. 189S, 800 u). This admixture was incubated at 37° C. for 3 hrs., followed by the addition of 120λ of 3M NaOAC and 12λ of 10% SDS. The admixture was transferred to 2 vortex tubes and 500λ of phenyl/CHCl$_3$/isoamyl was added to each, followed by a sec. vortex and 1 min. spin (1700 RPM). The aqueous phase was removed from the tubes and segregated into 3 tubes, followed by the addition to each tube of −20° C. 100% ETOH, followed by 10 min. spin (13,000 RPM). Thereafter, −20° C. 70% ETOH was added to each tube, followed by 1 min. spin (13,000 RPM). The tubes were then placed in a Speed VAC™ for drying, followed by resuspension of the contents in 100λ TE in a sterile hood. Five microliters (5λ) of the resuspended DNA was admixed with 995λ of deionized water (1:200 dilution). An optical density reading was taken (OD=260) and the amount of DNA present was calculated to be 0.75 μg/λ. In order to utilize 25 μg of DNA for electroporation, 32λ of the 1:200 dilution of the DNA was utilized (25 μg was utilized as this was the amount of DNA utilized for TCAE 5.2 and ANEX 1 in the foregoing Example 1). The 1:200 dilution of DNA was formally referred to as "Stu 1, Not I cut anti-CD20 in ANEX 2 (25 μg) in TE" and generally referred to as "anti-CD20 in ANEX 2."

Host cells utilized was DG44 CHO ("CHO") (Bee, Urlaub, G. *Somatic Cell,* 1986 supra). One hundred milliliters of 6.6×10⁵ cells/ml (84%) were subjected to a 2 min. spin at 1000 RPM. These were washed with 50 ml sucrose buffered solution, followed by 5 min. spin at 1000 RPM; the material was then resuspended in 4.5 ml of the sucrose buffered solution. Thereafter, cells were counted and 0.4 ml of CHO cells (4.0×10⁶ cells) were admixed with 322 of the anti-CD20 in ANEX 2 in BTX sterile, disposable electroporation cuvettes. Electroporation settings were as follows: 210 volts; 400 microfaraday capacitance; 13 ohms resistance, using a BTX $_{600}$™ electro cell manipulator (BTX, San Diego, Calif.). Nine (9) electroporations were conducted; actual voltage delivered over actual times were as follows: 1–199V, 4.23 msec; 2–188V, 4.57 msec; 3–189V, 4.24 msec, 4–200V; 4.26 msec, 5–200V, 4.26 msec; 6–199V, 4.26 msec; 7–189V, 4.59 msec; 8–189V, 4.57 msec; 9–201 V, 4.24 msec. (As noted in Example I, the difference in number of performed electroporations was attributed to the need to achieve a statistically significant number of viable colonies for each of the three conditions, TCAE 5.2, ANEX 1 and ANEX 2; the amount of DNA used for each electroporation (25 μg) was the same for each, and the same number of cells were electroporated.

Thereafter, the electroporation material was admixed with 20 ml of G418 Growth Media (CHO-S-SFM II minus hypoxanthine and thymidine (Gibco, Grand Island, NT, Form No. 91-0456PK)including 50 μM hypoxanthine and 8 μM thymidine). The admixture was gently agitated, followed by plating 200 μl of the admixture per well into 96-well plates, one plate for each electroporation (nine). Beginning on day 2 after electroporation, through day 17, 150 μl of each well was removed, and 150 μl of fresh G418 Growth Media containing 400 μg/ml G418 was added thereto. Colonies were analyzed on day 25.

One hundred and twenty one (121) colonies expressed anti-CD20 antibody (ie, 13 colonies per electroporation), Of these, 63 (52%) expressed over 250 μg /ml of protein; of the 63, 20 of the colonies (16.5%) expressed over 1000 μg/ml of protein. Only 5 of the 121 colonies (4.1%) expressed less than 25 μg/ml of protein. FIG. provides a histogram comparing expression of protein per colonies derived from the vectors TCAE 5.2, ANEX 1 and ANEX 2.

The foregoing data indicates that, inter alia, as between ANEX 1 and ANEX 2, the use of at least one out-of-frame start codon upstream of a fully impaired consensus Kozak associated with the translation initiation of a dominant selectable marker decreases the number of viable colonies expressing co-linked gene product and significantly increases the amount of expressed co-linked gene product.

III. Impact of Insertion of Gene Product of Interest within at Least One Artificial Intronic Insertion Region of a Dominant Selectable Marker Building further upon the ANEX 2 vector, an artificial splice was generated between amino acid residues 51 and 52 of the NEO coding region of ANEX 2, followed by insertion therein of the anti-CD20 encoding region. Two such vectors were generated: the first, comprising a consensus Kozak sequence for the NEO translation initiation codon and not comprising an out-of-frame start codon, is referred to as "GKNEOSPLA3F;" the second, comprising a fully impaired consensus Kozak and an out-of frame start condon, is referred to as "NEOSPLA3F."

Both GKNEOSPLA3F and NEOSPLA3F contain the following artificial intron sequence between amino acid residues 51 and 52 of NEO:

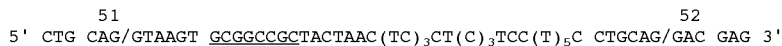

```
                 51                                                              52
         5' CTG CAG/GTAAGT GCGGCCGCTACTAAC(TC)₃CT(C)₃TCC(T)₅C CTGCAG/GAC GAG 3'
```

The underlined portion represents a sequence amenable to digestion with Not I enzyme; the encoding region for anti-CD20, inter alia, was inserted within this region.

Although not wishing to be bound by any particular theory, the inventor postulates that during expression, the inclusion of a gene product of interest within an artificial intronic insertion region of a dominant selectable marker (e.g. the NEO gene) should significantly decrease the number of viable colonies producing, in the case of the disclosed GKNEOSPA3F and NEOSPLA3F vectors, anti-CD20 antibody. This is predicated upon two points: first, only those vectors which are able to transcribe and correctly splice-out the antibody encoding region and correctly translate NEO will be G418 resistant; second, because each antibody cassette has its own promoter and polyadenylation region, transcription and translation of the antibody is independent of translation of NEO.

The GKNBOSPLA3F and NEOSPLA3F vectors were constructed in the following manner:

Anti-CD20 in ANEX 2 was digested with Not I and Xho I in order to isolate the 1503 bp NEO cassette DNA fragment (see FIG. 4 between "Not I 7023" and "Xho I 5520") as follows: 10 μl of anti-CD20 in ANEX 2 was admixed with 6 μl deionized H$_2$O ("dH2O"); 1 μl Not I enzyme (NEB, Prod. No. 189S); 2 μl of 10× Not I digestion buffer (NEB; provided with enzyme); and 1 μl Xho I enzyme (Promega, Madison, Wis., Prod. No. R4164). This digestion mixture was incubated overnight at 37° C. The resulting digested DNA was size fractionated by 0.8% agarose gel electrophoresis and the desired fragment migrating at 1503 was isolated via the GlassMAX™ method (Gibco BRL, Grand Island, N.Y., Prod. No. 15590-011) for insertion into pBluescript SK(−) plasmid DNA (Stratagene, La Jolla, Calif.).

Bluescript SK (−) was previously prepared for acceptance of the NEO cassette by double digestion with Not I and Xho I using the same conditions as above for anti-CD20 in ANEX 2. Digested pBluescript SK (−) was then collected by ethanol precipitation by the addition of 70 μl dH20; 2 μl tRNA (Sigma, St. Louis, Mo., Prod. No. R-8508); 10 μl of 3M NaOAc; and 300 μl 100% ETOH (−20° C.). This was followed by a 10 min spin (13,000 RPM), decanting the supernatant, rinsing with 70% ETOH, decanting the liquid, drying in a SpeedVAC™ and resuspending in 20 μl 1× TE.

Ligation of the NEO cassette DNA fragment into prepared pBluescript SK (−) vector was accomplished as follows: 10 μl of NEO fragment DNA was admixed with 6 μl dH$_2$O; 1 μl cut pBluescript SK (−) vector DNA; 2 μl 10× ligation buffer (Promega, supplied with enzyme); and 1 μl T-4 DNA Ligase (Promega, Prod. No. M1801) followed by incubation at 14° C. overnight. Ligated DNA was collected by ethanol precipitation as described above for the preparation of pBluescript SK (−) vector DNA.

Ten (10) μl of the resuspended ligated DNA was transformed into *E. coli* XL-1 Blue™ (Stratagene), following manufacturer instructions. Ten (10) bacterial colonies were inoculated in LB broth (Gibco BRL, Prod. No. M27950B) including ampicillin (50 μg/ml; Sigma, Prod. No. A-9393). Plasmids were isolated from the cultures with a Promega DNA purification system (Prod. No. PR-A7100), following manufacturer instructions; these plasmids may have comprised the plasmid referred to as BlueNEO+ depending on the sufficiency of the foregoing. (BlueNEO+ was confirmed due to the sufficiency of the following procedure.)

BlueNEO+ contains a Not I restriction recognition sequence reformed upon ligation of the NEO cassette fragment DNA into the pBluescript SK (−) vector. This site was destroyed by the following: 1 μl of BlueNEO+ DNA was admixed with 16 μl dH$_2$O; 2 μl 10× Not I digestion buffer (NEB); 1 μl Not I enzyme (NEB). This was followed by incubation at 37° C. for 2 hrs. This digested DNA was then purified by spin column fractionation resulting in 15 μl final volume. This 15 μl Not I digested DNA was "blunt-ended" by admixing with 4 μl 5' Klenow buffer (20 mM Tris-HCL, pH 8.0, 100 mM MgCl$_2$) and 1 μl DNA Polymerase I Large (Klenow) Fragment (Promega, Prod. No. M2201). This admixture was incubated at room temperature for 30 minutes. Blunt-ended DNA was then purified by spin column fractionation, giving a final volume of 15 μl.

Ligation of the blunt-ended DNA was performed in an analogous way as to the ligation of the NEO cassette fragment DNA into the pBluescript SK (−) vector except that the final DNA was resuspended in 17 μl of 1× TE.

Following ligation, the DNA was subjected to a second restriction digestion with Not I by mixing the 17 μl of DNA with 2 μl 10× Not I digestion buffer and 1 μl Not I enzyme (NEB). Digestion was allowed to proceed at 37° C. for 60 minutes. Following digestion, the admixture was purified by spin column fractionation resulting in 15 μl final volume.

Ten (10) μl of the purified DNA was transformed into *E. coli* XL-1 Blue™ (Stratagene), following manufacturer instructions. Ten (10) bacterial colonies were inoculated in LB broth (Gibco BRL including ampicillin (50 μg/ml; Sigma). Plasmids were isolated from the 10 cultures with a Promega DNA purification system following manufacturer instructions; these plasmids may have comprised the plasmid referred to as BlueNEO− depending on the sufficiency of the foregoing. (BlueNEO− was confirmed due to the sufficency of the following procedure.)

BlueNEO− contains a unique Pst I restriction site spanning the codons for amino acid residues 51 and 52. BlueNEO− was digested with Pst I as follows: an admixture was formed containing 15 μl dH$_2$O; 1 μl BlueNEO− DNA, 2 μl digestion buffer 3 (NEB) and 2 μl Pst I enzyme (NEB, Prod. No. 140S). This admixture was incubate at 37° C. for 3 hrs. Digested DNA was then purified by spin column fractionation. The following synthetic oligonucleotide was then ligated to the Pst I cohesive ends of BlueNEO−:

5'GGTAAGTGCGGCCGCTACTAACTCTCTC-CTCCCTCCTTTTCCTGCA 3' (SEQ ID NO: 12) and its complementary sequence:

5'GGAAAAAGGAGGGAGAGAGTTACTAGCG-GCCGCAMTTACCTGCA 3' (SEQ ID NO: 13).

Insertion of this linker creates a consensus 5' splice donor site (by ligation) followed by a Not I site, followed by a consensus splice branch point, followed by a synthetic polypyrimidine tract, followed by a consensus 3' splice acceptor site, as indicated above.

Ligation was performed as described above for the ligation of the NEO cassette into pBluescript SK (−) except using 2 μl of Pst I linearized BlueNEO− DNA and 14 μl (175 pmoles) of annealed complementary oligonucleotides.

The foregoing (and following) synthetic oligo nucleotides were chemically synthesized using an Applied Biosystems 391 PCR MATE™ DNA Synthesizer (Applied Biosystems, Foster City, Calif.). All reagents for the synthesis were purchased from Applied Biosystems.

Ligated DNA was collected by ethanol precipitation as described above for the preparation of pBluescript SK (−) vector DNA.

Ten (10) μl of the resuspended ligated DNA was transformed into *E. coli* XL-1 Blue™ (Stratagene), following manufacturer instruction. Ten (10) bacterial colonies were inoculated in LB broth (Gibco BRL) including ampicillin (50 μg/ml; Sigma). Plasmids were isolated from the 10 cultures with a Promega DNA purification system, following manufacturer instructions; these plasmids may have comprised the plasmid referred to as NEOSPLA and/or NEOSPLA-depending on the sufficiency of the foregoing and the orientation of the insertion of the oligonucleotides.

Determination of orientation of the splice junction linker was preformed by nucleic acid sequencing using the Sequenase Version 2.0 DNA Sequencing Kit (United States Biochemical, Cleveland, Ohio, Prod. No. 70770) following manufacturer instructions. Upon determination of linker orientation within six independent plasmid isolates, identification of NEOSPLA was made such that the inserted splice junction sequences are in the correct forward orientation with respect to the direction of NEO transcription.

NEOSPLA was digested with Xho I by forming an admixture of 15 μl dH$_2$O; 1 μl NEOSPLA DNA; 2 μl 10× digestion buffer D (Promega, supplied with enzyme); and 2 μl Xho I enzyme (Promega, Prod. No. R6161). This admixture was digested at 37° C. for 3 hrs followed by DNA purifcation by spin column fractionation. Into this site was ligated a self complementary synthetic oligonucleotide having the following sequence: 5'TCGA<u>TTAATTAA</u> 3' (SEQ ID NO: 14). Insertion of this sequence effectively changes the Xho I site to a Pac I restriction site (as underlined in SEQ ID NO: 14).

Ligation was performed as described above for the ligation of the NEO cassette into pBluescript SK (−) except using 2 μl of Xho I linearized NEOSPLA DNA and 14 μl (175 pmoles) of annealed complementary oligonucleotides.

Ligated DNA was collected by ethanol precipitation as described above for the preparation of pBluescript SK (−) vector DNA.

Ten (10) μl of the resuspended ligated DNA was transformed into E. coli XL-1 Blue™ (Stratagene), following manufacturer instructions. Ten (10) bacterial colonies were inoculated in LB broth (Gibco BRL) including ampicillin (50 μg/ml; Sigma). Plasmids were isolated from the 10 cultures with a Promega DNA purification system, following manufacturer instructions; these plasmids may have comprised the plasmid referred to as NEOSPLA3 depending on the sufficiency of the foregoing. (NEOSPLA3 was confirmed due to the sufficency of the following procedure.)

Anti-CD20 in ANEX 2(G1,K) contains the anti-CD20 light chain and heavy chain immunoglobulin cassettes and a DHFR cassette bounded by a Not I site at the 5' end and an Xho I site at the 3' end. Anti-CD20 in ANEX 2(G1,K) was digested with Xho I by forming an admixture of 15μldH$_2$O, 1 μl anti-CD20 in ANEX 2(G1,K) DNA, 2 μl 10x digestion buffer D (Promega, supplied with enzyme) and 2 μl Xho I enzyme (Promega, Prod. No. R6161). This admixture was digested at 37° C. for 3 hrs followed by DNA purifcation by spin column fractionation. Into this site was ligated a self complementary synthetic oligonucleotide of the following sequence: 5'TCGAA<u>GCGGCCGC</u>T 3" (SEQ ID NO: 15). Insertion of this sequence effectively changes the Xho I site to a Not I restriction site (as underlined in SEQ ID NO: 15).

Ligation was performed as described above for the ligation of the NEO cassette into pBluescript SK (−) except using 2 μl of Xho I linearized anti-CD20 in ANEX 2 DNA and 14 μl (175 pmoles) of annealed complementary oligonucleotides.

Ligated DNA was collected by ethanol precipitation as described above for this preparation of pBluescript SK (−) vector DNA.

Ten (10) μl of the resuspended ligated DNA was transformed into E. coli XL-1 Blue™ (Stratagene), following manufacturer instructions. Ten (10) bacterial colonies were inoculated in LB broth (Gibco BRL, Prod. No. M27950B) including ampicillin (50 μg/ml; Sigma, Prod. No. A-9393). Plasmids were isolated from the cultures with a Promega DNA purification system (Prod. No. PR-A7100), following manufacturer instructions; these plasmids may have comprised the plasmid referred to as Anti-CD20 in ANEX 2(G1,K)A depending on the sufficiency of the foregoing. (This was confirmed due to the sufficiency of the following procedure.)

Anti-CD20 in ANEX 2(G1,K)A was digested with Not I and Xho I by forming an admixture of 6 μl dH$_2$O; 10 μl Anti-CD20 in ANEX 2(G1,K); 2 μl 10x Not I digestion buffer (NEB, supplied with Not I enzyme); and 1 μl Not I enzyme (NEB). This admixture was digested at 37° C. for 3 hrs followed by size fractionation by 0.8% agarose gel electrophoresis and the desired fragment migrating at 5515 base pairs by was isolated via the GlassMAX method for insertion into NEOSPLA3.

NEOSPLA3 was previously prepared for acceptance of the anti-CD20 cassette by digestion of 1 μl of DNA with Not I using an admixture comprising 16 μl dH$_2$O; 2 μl 10x Not I digestion buffer (NEB); 1 μl Not I enzyme (NEB); followed by incubation at 37° C. for 2 hrs. This digested DNA was then purified by spin column fractionation resulting in 15 μl final volume.

Ligation of the anti-CD20 DNA fragment into prepared NEOSPLA3 vector was accomplished as follows: 10 μl of anti-CD20 fragment DNA was admixed with 6 μl dH$_2$O; 1 μl cut NEOSPLA3 vector DNA; 2 μl 10x ligation buffer (Promega supplied with enzyme); and 1 μl T4 DNA Ligase (Promega); followed by incubation at 14° C. overnight. Ligated DNA was collected by ethanol precipitation as described above for the preparation of pBluescript SK (−) vector DNA.

Ten (10) μl of the resuspended ligated DNA was transformed into E. coli XL-1 Blue™ (Stratagene), following manufacturer instructions. Ten (10) bacterial colonies were inoculated in LB broth (Gibco BRL) including ampicillin (50 μg/ml; Sigma). Plasmids were isolated from the 10 cultures with a Promega DNA purification system following manufacturer instructions; these plasmids may have comprised the plasmids referred to as anti-CD20 in NEOSPLA3F and anti-CD20 in NEOSPLA3R depending on the sufficiency of the foregoing and relative orientation of the inserted fragment with respect to NEO transcription.

Determination of orientation of the anti-CD20 cassette insertion was preformed by double digestion with KpnI and SpeI (NEB, Prod. No. 1335) in NEB buffer 1 plus acetated BSA as follows: an admixture comprising 4 0 DNA; 2 μl NEB buffer 1; μl Kpn I; 1 μl Spe I; 2 μl BSA; and 10 μl dH$_2$O was formed. The admixture was digested at 37° C. for 2 hrs, followed by size fractionation on an 0.8% agarose gel electrophoresis. Upon determination of anti-CD20 insert orientation within six independent plasmid isolates, identification of anti-CD20 in NEOSPLA3F was made such that the inserted sequences are in the forward orientation with respect to the direction of NEO transcription.

The 5515 bp anti-CD20 fragment contains the SV40 origin, a chimeric mouse human immunoglobulin light chain transcriptional cassette, a chimeric mouse human immunoglubulin heavy chain transcriptional cassette, and a murine dihydrofolate reductase transcriptional cassette (see, FIG. 4).

Anti-CD20 in NEOSPLA3F was doubly digested with Kpn I and Stu I by creating the admixture consisting of 14 μl dH$_2$O, 1 μl anti-CD20 in NEOSPLA3F, 2 μl 10x digestion buffer 1 (NEB, supplied with enzyme), 2 μl 10x acetylated BSA (NEB supplied with Kpn I enzyme), 1 μl Kpn I enzyme, 1 μl Stu I enzyme (NEB, Prod. Nos. 142S and 187S respectively). This admixture was digested at 37° C. for 3 hrs followed by size fractionation by 0.8% agarose gel electrophoresis and the desired fragment migrating at 9368 base pairs by was isolated via the GlassMAX method.

A PCR fragment of DNA was generated from TCAE 5.2. The two following synthetic oligonucleotide primers were utilized in the PCR reaction:

5' primer: 5' GCA TGC <u>GGT ACG</u> GGA TCC ATC GAG CTA CTA GCT TTG C 3' (SEQ ID NO: 16);

3' primer: 5' CTG ACT AGG <u>CCT</u> AGA GCG GCC GCA CTT ACC TGC AGT TCA TCC AGG GC 3' (SEQ ID NO: 17)

The underlined portion of SEQ ID NO: 16 represents a Kpn I site, and the underlined portion of SEQ ID NO: 17 represents a Stu I site.

The PCR product was digested with Kpn I and Stu I and then ligated into prepared anti-CD20 in NEOSPLA3F.

Ligation of the 627 bp fragment into prepared anti-CD20 in NEOSPLA3F was accomplished as follows:

2 μl anti-CD20 in NEOSPLA3F; 1 μl SDS; 1 μl tRNA (Sigma); 11 μl 3M sodium acetate (pH 4.5) were admixed. Following phenol/chloroform isoamyl extraction of the admixture, the DNA was precipitated from the aqueous phase by addition of 270 μl ethanol (ice-cold) and this was spun at 13,000 rpm for 10 min. Following a 70% ETOH wash, the DNA was resuspended in 16 μlTE, 10 μl of PCR fragment DNA was admixed with 6 μl dH$_2$O, 1 μl cut anti-CD20 in NEOSPLA3F vector DNA, 2 μl 10× ligation buffer (Promega, supplied with enzyme) and 1 μl T-4 DNA Ligase (Promega) followed by incubation at 14° C. overnight. Ligated DNA was collected by ethanol precipitation as described above for the preparation of pBluescript SK (−) vector DNA.

Ten (10) μl of the resuspended ligated DNA was transformed into *E. coli* XL-1 Blue™ (Stratagene), following manufacturer instructions. Ten (10) bacterial colonies were inoculated in LB broth (Gibco BRL, Prod. No. M27950B) including ampicillin (50 μg/ml; Sigma, Prod. No. A-9393). Plasmids were isolated from the cultures with a Promega DNA purification system (Prod. No. PR-A7100), following manufacturer instructions; these plasmids may have comprised the plasmid referred to as anti-CD20 in GKNEOSPLA3F depending on the sufficiency of the foregoing. (Confirmation was based upon sequence determination of the different regions of GKNEOSPLA3F vs. NEOSPLA3F.)

The new plasmid differs from anti-CD20 in NEOSPLA3F in its Kozak sequence for the NEO gene which is:

```
                         -3       +1
TGT GTT GGG AGC TTG GAT CGAT cc Acc ATG Gtt
                     Cla I         Start NEO for Anti-CD20 in GKNEOSPLA3F, and -3         +1
TGT G CCA GCA TGG AGG AAT CGA Tcc Tcc ATG Ctt
         upstream Start            Start NEO
``` for Anti-CD20 in NEOSPLA3F.

Comparative analysis of expression of anti-CD20 in TCAE 5 vector (comprising NEO with consensus Kozak); ANEX 2 vector (comprising NEO with fully impaired Kozak, and upstream out-of-frame start sequence); NEOPLA3F (anti-CD20 inserted via artificial intronic insertion region between amino acids 51 and 52 of NEO; NEO has fully impaired Kozak and an upstream out-of-frame start sequence); and GKNEOSPLA3F (anti-CD20 inserted via artificial intronic insertion region between amino acids 51 and 52 of NEO; NEO has consensus Kozak).

Twenty-five (25) μg of each plasmid (digested as follows: anti-CD20 in TCAE5 and ANEX2-Not I; anti-CD20 in NEOSPLA3F-Pac I; anti-CD20 in GKNEOSPLA3F-Pac I and Kpn I) was electroporated into 4×10$^6$ CHO cells; these digestions were utilized to separate the genes expressed in mammalian cells from the DNA used to grow the plasmid in bacteria. Following digestion, EtOH precipitation of the DNA, and drying thereof, the DNA was resuspended in sterile TE at a concentration of 1 μg/μl. Electroporation conditions were as described in Example II, except that 230 volts was utilized and, following electroporation, the mixture of cells and DNA was maintained for 10 min. at room temperature in the sterile, disposable electroporation cuvette.

Following electroporation, cells were plated into 96 well dishes as shown below in Table I, based upon the expected frequency of G418 resistant colonies (as derived from preliminary experiments; data not shown):

TABLE I

COMPARATIVE EXPRESSION

| Plasmid | No. Transfections | No. Cells Plated | No. 96 Well Plates |
|---|---|---|---|
| TCAE 5 | 1 | 4 × 10$^5$ | 5 |
| ANEX 2 | 1 | 2 × 10$^6$ | 5 |
| GKNEOSPLA3F | 1 | 2 × 10$^6$ | 5 |
| NEOSPLA3F | 5 | 2 × 10$^7$ | 5 |

| Plasmid | No. G418 Resistant Colonies | Frequency of G418 Resistant Colony per Transfected Cell |
|---|---|---|
| TCAE 5 | 16 | 1 in 20,000 |
| ANEX 2 | 16 | 1 in 100,000 |
| GKNEOSPLA3F | 16 | 1 in 100,000 |
| NEOSPLA3F | 16 | 1 in 1,000,000 |

(Cells were fed with G418 containing media on days 2, 5, 7, 9, 12, 14, 18, 22, 26, 30 and 34; supernatant from colonies was assayed for immunoglobulin production and the colonies became confluent in the wells on days 18, 22, 26, 30 and 34).

Figure 7A:
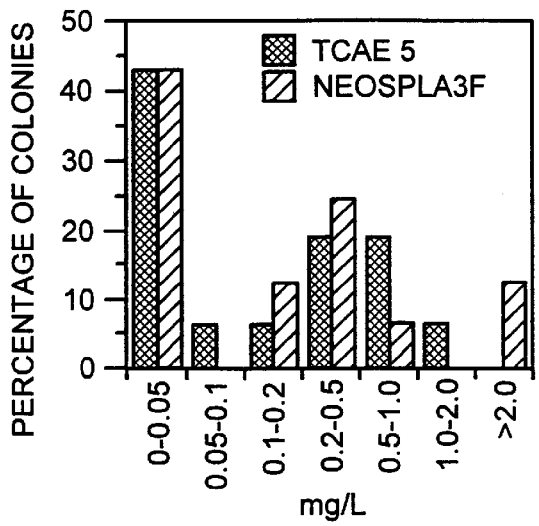
FIGS. 7A, 7B and 7C are histograms comparing protein expression levels with the vectors TCAE 5.2 vs. NEOSPLA 3F (7A). ANEX 2 vs. NEOSPLA3F (7B); and GK-NEOSPLA3F vs. NEOSPLA3F (7C).
Figure 7B:
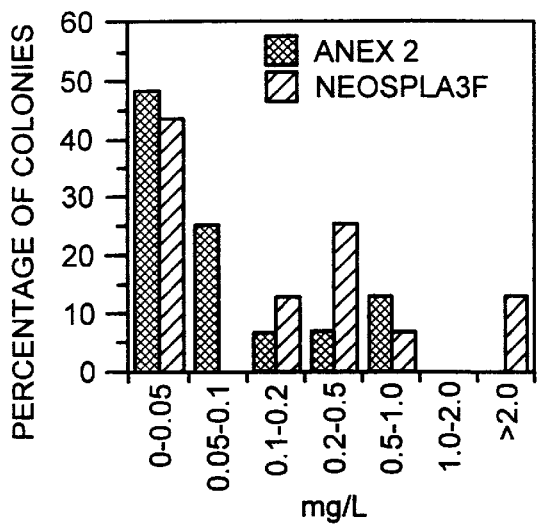
Figure 7C:
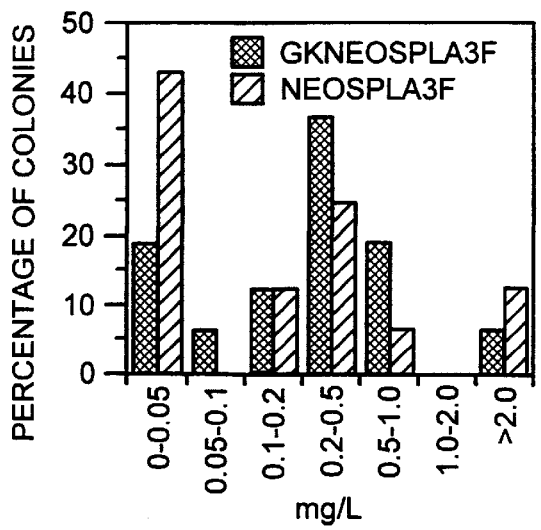

FIGS. 7A to 7C provide histogram results and evidence the percentage of colonies at a particular level of expression.

The Examples provided herein are not to be construed as limited to the specific vectors, fully impaired consensus Kozak sequences, dominant selectable markers, transcriptional cassettes, and/or expressed proteins. The fully impaired consensus Kozak, and the utilization thereof, are not to be construed as limited to ANEX 1 and ANEX 2 vectors. Similarly, the preferred fully impaired consensus Kozak sequences and vectors in no way constitute an admission, either actual or implied, that these are the only sequences or vectors to which the inventor is entitled. The inventor is entitled to the full breadth of protection under applicable patent laws. Preferred vectors incorporating fully impaired consensus Kozak sequences have been identified by the inventor on ANEX 1 and ANEX 2 for purposes of claiming these vectors by designating plasmids comprising these vectors and anti-CD20 were deposited with the American Type Culture Collection (ATCC), 12301 Parklawn Drive, Rockville, Md., 20852, under the provisions of the Budapest Treaty for the International Recognition of the Deposit of Microorganisms for the Purpose of Patent Procedure. The plasmids were tested by the ATCC on Nov. 9, 1992, and determined to be viable on that date. The ATCC has assigned these plasmids the following ATCC deposit numbers 69120 (anti-CD20 in TCAE 12(ANEX 1)) and 69118 (anti-CD20 in ANEX 2 (G1,K)); for purposes of this deposit, these plasmids were transformed into *E. coli*.

Although the invention has been described in considerable detail with regard to certain preferred embodiments thereof, other embodiments within the scope of the teachings of the present invention are possible. Accordingly, neither the disclosure nor the claims to follow, are intended, nor should be construed to be, limited by the descriptions of the preferred embodiments contained here.

What is claimed is:

1. A method for expressing an immunoglobulin protein or antigen binding fragment thereof comprising (1) transforming a mammalian cell with an expression vector comprising (a) a dominant selectable marker wherein the translation initiation start site of said marker comprises the following sequence:

$$-3 \quad +1$$
$$\text{Pyxx ATG Pyxx}$$

wherein "Py" is a pyrimidine nucleotide, "x" is a nucleotide, and the numerical designations are relative to the codon "ATG", and (b) a DNA sequence or sequences encoding said immunoglobulin protein or fragment thereof, wherein said DNA sequence or sequences are operably linked to regulatory sequences that provide for the expression of said immunoglobulin protein or fragment thereof in a mammalian cell transformed with said expression vector;

(2) and culturing the resultant transformed mammalian cell under conditions that provide for the expression of said immunoglobulin or fragment thereof.

2. The method of claim 1 wherein said dominant selectable marker is selected from the group consisting of: herpes simplex virus thymidine kinase, adenosine deaminase, asparagine synthetase, Salmonella his D gene, xanthine guanine phosphoribosyl transferase, hygromycin B phosphotransferase, and neomycin phosphotransferase.

3. The method of claim 1 wherein said translation initiation start site sequence is selected from the group consisting of TxxATGCxx; CxxATGCxx; CxxATGTxx; and TxxATGTxx, wherein "x" is a nucleotide, with the proviso that the codon "Txx" downstream of the ATG codon does not encode a stop codon.

4. The method of claim 1 wherein said translation initiation start site sequence is TxxATGCxx, where "x" is a nucleotide.

5. The method of claim 1 wherein said translation initiation start site sequence is TCCATGCTT.

6. The method of claim 1 wherein said translation initiation start site sequence is located within a secondary structure.

7. The method of claim 1 wherein said translation initiation start site sequence further comprises at least one out-of-frame start codon within about 1000 nucleotides of the ATG start codon of said start site, with the proviso that no in-frame stop codon is located within said 1000 nucleotides.

8. The method of claim 1 wherein said translation initiation start site sequence further comprises at least one out-of-frame start codon within about 350 nucleotides of the ATG start codon of said start site, with the proviso that no-inframe stop codon is located within said 350 nucleotides.

9. The method of claim 1 wherein said translation initiation start site sequence further comprises at least one out-of-frame start codon within about 50 nucleotides of the ATG start codon of said start site, with the proviso that no in-frame stop codon is located within said 50 nucleotides.

10. The method of claim 7 wherein said out-of-frame start codon is part of a consensus Kozak sequence.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: misc_feature
          (B) LOCATION: 11..18
          (D) OTHER INFORMATION: /note= "Nucleotides 11, 12, 17 and
               18 are "N" wherein "N" represents a nucleotide."

(xi) SEQUENCE DESCRIPTION: SEQ ID NO:1:

GACCATGGCC NNATGCNN                                                      18

(2) INFORMATION FOR SEQ ID NO:2:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:2:

TAGCTAGGTC CTACCCC                                                       17

(2) INFORMATION FOR SEQ ID NO:3:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:3:

ATCGATCCTG GATGCGG                                                       17

(2) INFORMATION FOR SEQ ID NO:4:

(i) SEQUENCE CHARACTERISTICS:
          (A) LENGTH: 11 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:4:

CGCGTATGGC T                                                             11

(2) INFORMATION FOR SEQ ID NO:5:

(i) SEQUENCE CHARACTERISTICS:
          (A) LENGTH: 11 base pairs
          (B) TYPE: nucleic acid
          (C) STRANDEDNESS: single -continued (D) TOPOLOGY: linear (ii) MOLECULE TYPE: DNA (genomic)

(xi) SEQUENCE DESCRIPTION: SEQ ID NO:5:

GCAGAATGTT A                                                    11

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAGATATGAA A                                                    11

(2) INFORMATION FOR SEQ ID NO:7:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TTCACATGAG C                                                    11

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GAACCATGGC C                                                    11

(2) INFORMATION FOR SEQ ID NO:9:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCACCATGTG T                                                    11

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GGATGGGGAT CGTTTCGCAT GATT                                              24

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCATGCCATG GCCNNATGCN N                                                 21

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

NATGNNNNNN NTNNATGCNN                                                   20

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..12

(xi) SEQUENCE DESCRIPTION: SEQ ID NO:13:

CTG CAG GAC GAG                                                         12
Leu Gln Asp Glu
  1

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 22
        (D) OTHER INFORMATION: /note= "Nucleotide 22 is N wherein
            N = (TC)3."

(ix) FEATURE:
        (A) NAME/KEY: misc_feature
        (B) LOCATION: 25
        (D) OTHER INFORMATION: /note= "Nucleotide 25 is N wherein
            N = (C)3."

(ix) FEATURE:
        (A) NAME/KEY: misc_feature
        (B) LOCATION: 29
```

(D) OTHER INFORMATION: /note= "Nucleotide 29 is N wherein
                N = (T)5."

(xi) SEQUENCE DESCRIPTION: SEQ ID NO:14:

GTAAGTGCGG CCGCTACTAA CNCTNTCCNC CTGCAG                                36

(2) INFORMATION FOR SEQ ID NO:15:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

TTGGGAGCTT GGATCGATCC ACCATGGTT                                        29

(2) INFORMATION FOR SEQ ID NO:16:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

TTGGGAGCTT GGATCGATCC TCCATGCTT                                        29

(2) INFORMATION FOR SEQ ID NO:17:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

CCAGCATGGA GGAATCGATC CTCCATGCTT                                       30

(2) INFORMATION FOR SEQ ID NO:18:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

CCAGCATGGA GGAATCGATC CTCCATGCTT G                                     31

(2) INFORMATION FOR SEQ ID NO:19:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

```
GGAGGATCGA TTCCTCCATG CTGGCACAAC TATGTCAGAA GCAAATGTGA GC                    52
```

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CTGGGGCTCG AGCTTTGC                                                        18
```

(2) INFORMATION FOR SEQ ID NO:21:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..48
        (D) OTHER INFORMATION: /note= "Nucleotide 28 wherein N =
            TC3."

(ix) FEATURE:
        (A) NAME/KEY: misc_feature
        (B) LOCATION: 1..48
        (D) OTHER INFORMATION: /note= "Nucleotide 31 wherein N =
            C3."

(ix) FEATURE:
        (A) NAME/KEY: misc_feature
        (B) LOCATION: 1..48
        (D) OTHER INFORMATION: /note= "Nucleotide 35 wherein N =
            T5."

(xi) SEQUENCE DESCRIPTION: SEQ ID NO:21:

```
CTGCAGGTAA GTGCGGCCGC TACTAACNCT NTCCNCCTGC AGGACGAG                       48
```

(2) INFORMATION FOR SEQ ID NO:22:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GGTAAGTGCG GCCGCTACTA ACTCTCTCCT CCCTCCTTTT TCCTGCA                        47
```

(2) INFORMATION FOR SEQ ID NO:23:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
GGAAAAAGGA GGGAGGAGAG AGTTAGTAGC GGCCGCACTT ACCTGCA                        47
```

(2) INFORMATION FOR SEQ ID NO:24:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TCGATTAATT AA                                                           12

(2) INFORMATION FOR SEQ ID NO:25:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TCGAAGCGGC CGCT                                                         14

(2) INFORMATION FOR SEQ ID NO:26:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GCATGCGGTA CCGGATCCAT CGAGCTACTA GCTTTGC                                37

(2) INFORMATION FOR SEQ ID NO:27:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CTGACTAGGC CTAGAGCGGC CGCACTTACC TGCAGTTCAT CCAGGGC                     47

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TGTGTTGGGA GCTTGGATCG ATCCACCATG GTT                                    33

(2) INFORMATION FOR SEQ ID NO:29:

(i) SEQUENCE CHARACTERISTICS:
        (A) LENGTH: 34 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

TGTGCCAGCA TGGAGGAATC GATCCTCCAT GCTT                                  34

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 24..29

(xi) SEQUENCE DESCRIPTION: SEQ ID NO:30:

TTGGGAGCTT GGATCGATCC ACC ATG GTT                                      29
                         Met Val
                           5

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 24..29

(xi) SEQUENCE DESCRIPTION: SEQ ID NO:31:

TTGGGAGCTT GGATCGATCC TCC ATG CTT                                      29
                         Met Leu (2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 25..30

(xi) SEQUENCE DESCRIPTION: SEQ ID NO:32:

CCAGCATGGA GGAATCGATC CTCC ATG CTT                                     30
                           Met Leu